United States Patent [19]

White

[11] Patent Number: 5,914,097
[45] Date of Patent: Jun. 22, 1999

[54] AMINO-ACYL-TYPE AND CATECHOLAMINE-TYPE CONTRAST AGENTS FOR MRI

[75] Inventor: David L. White, Oakland, Calif.

[73] Assignee: Regents of the University of California, Oakland, Calif.

[21] Appl. No.: 08/486,278

[22] Filed: Jun. 6, 1995

Related U.S. Application Data

[63] Continuation of application No. 08/169,301, Dec. 17, 1993, Pat. No. 5,562,894, which is a continuation-in-part of application No. 08/086,349, Jun. 30, 1993, abandoned, which is a continuation-in-part of application No. 07/927,172, Aug. 7, 1992, abandoned, which is a continuation-in-part of application No. 07/744,470, Aug. 12, 1991, abandoned, which is a continuation-in-part of application No. 07/743,143, Aug. 9, 1991, abandoned.

[51] Int. Cl.$^6$ .............................. A61B 5/055; C07F 5/00
[52] U.S. Cl. .................... 424/9.365; 514/492; 514/502; 514/836; 534/16; 556/50; 556/63; 556/107; 556/117; 556/134; 556/148
[58] Field of Search .......................... 424/9.365; 514/6, 514/492, 502, 836; 436/173, 806; 128/653.4, 654; 534/14, 16; 556/50, 63, 107, 117, 134, 148

[56] References Cited

U.S. PATENT DOCUMENTS

| 4,352,751 | 10/1982 | Wieder et al. | 530/303 |
| 4,647,447 | 3/1987 | Gries et al. | 424/9.36 |
| 4,863,717 | 9/1989 | Keana | 424/9 |
| 4,972,837 | 11/1990 | Engelstad et al. | 424/9.365 |
| 5,135,737 | 8/1992 | Keana | 424/9 |
| 5,138,040 | 8/1992 | Moore et al. | 424/9.365 |

FOREIGN PATENT DOCUMENTS

| 2045987 | 4/1971 | France . |
| 58-59954 | 4/1983 | Japan . |
| 7005293 | 3/1971 | South Africa . |
| WO 90/01024 | 2/1990 | WIPO . |
| WO 91/03200 | 3/1991 | WIPO . |
| WO 93/15771 | 8/1993 | WIPO . |
| WO 93/16375 | 8/1993 | WIPO . |

OTHER PUBLICATIONS

Janoki, G.Y.A., et al., "[$^{67}$Ga]Desferrioxamine–HSA: Synthesis of chelon protein conjugates using carbodiimide as a coupling agent" *Int. J. Radiat. Isot.* (1983) 34(6):871–877.

Rodgers, S.J., et al., "Ferric ion sequestering agents. 11. Synthesis and kinetics of iron removal from transferrin of catecholyl derivatives of desferrioxamine B$^1$" *J. Med. Chem.* (1983) 26:439–442.

Lempers et al., "A new trinuclear complex of platinum and iron efficiently promotes cleavage of plasmid DNA" *Nucl. Acids Res.* (1993) 21(8):1983–1990.

Virzi et al., "New Indium–111 labeled biotin derivatives for improved immunotargeting" *Nucl. Med. Biol.* (1991) 18(7):719–726.

*Primary Examiner*—Gary E. Hollinden, PH.D.
*Assistant Examiner*—Michael G. Hartley
*Attorney, Agent, or Firm*—Morrison & Foerster LLP

[57] ABSTRACT

The present invention relates to the preparation of amino-acyl-type and catecholamine-type compounds having multiple carboxylic acid functional groups. Paramagnetic metal (II) or (III) ion chelate complexes are formed using these compounds for use as intravenous contrast agents to produce enhanced contrast magnetic resonance images of the heart, liver, biliary tree or upper small intestine. The mono- and di-amino acids, their esters and amides, and catecholamine-like derivatives, of EDTA, DTPA, and the like are prepared. The paramagnetic metal (II) or (III) ion complexes are formed and produce T1-related contrast effects in MR images. The compounds and complexes also appear to have low toxicities and to be relatively rapidly and completely cleared from the tissue of a living mammal, e.g. a human being.

18 Claims, 17 Drawing Sheets

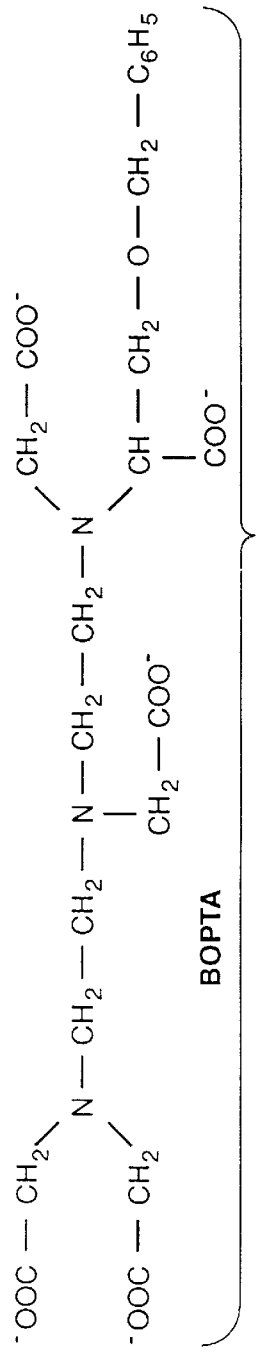
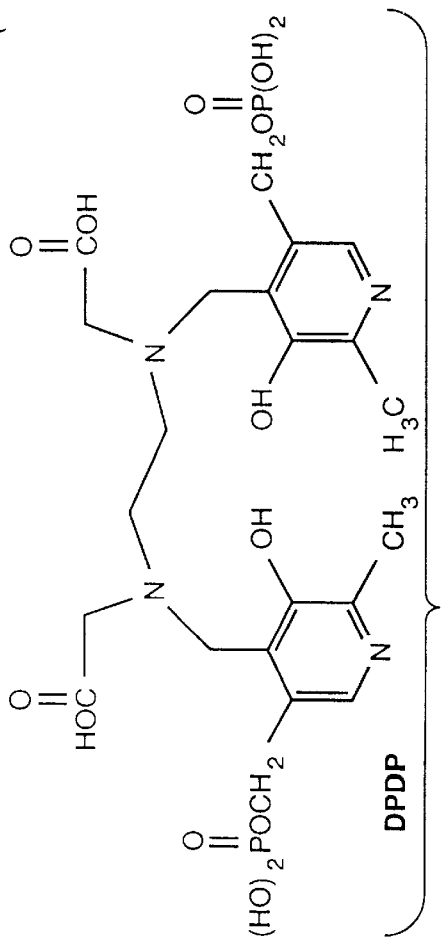
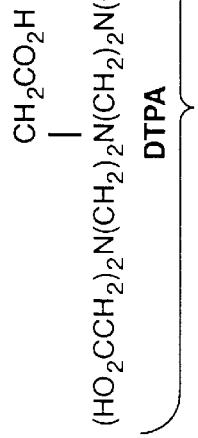
FIG. 1A (PRIOR ART) BOPTA
FIG. 1B (PRIOR ART) DPDP
FIG. 1C (PRIOR ART) Bromosulfophthatein (BSP)
FIG. 1D (PRIOR ART) DTPA

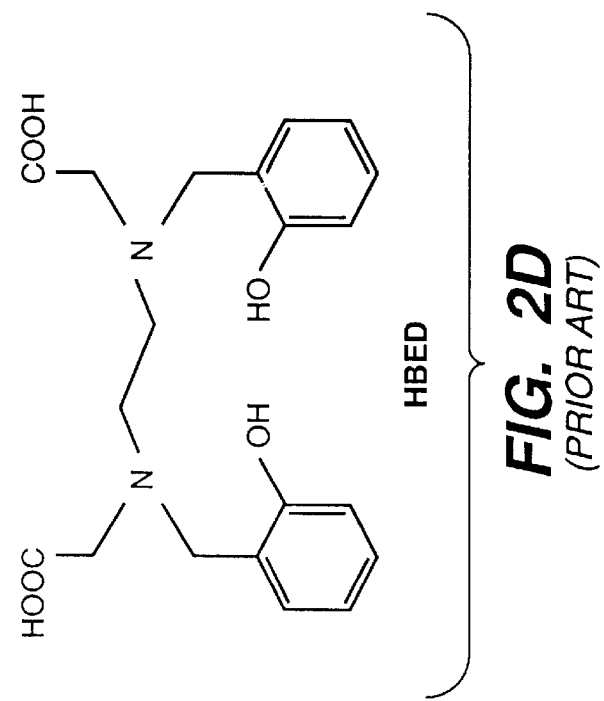
FIG. 2B *(PRIOR ART)*
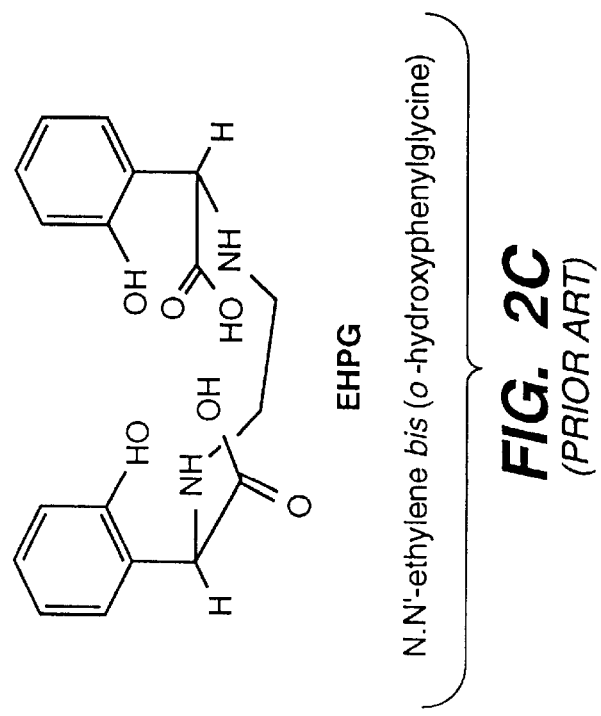
FIG. 2D *(PRIOR ART)*
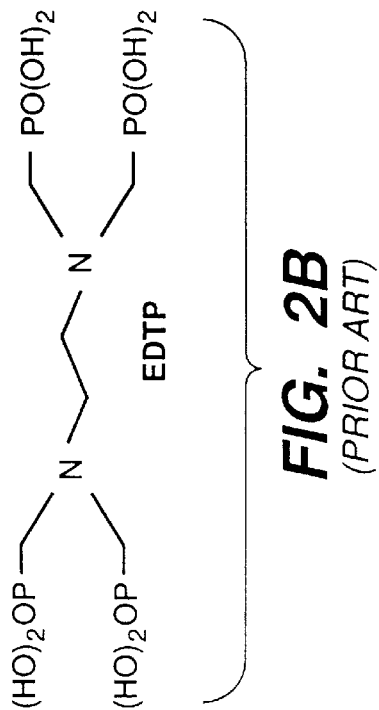
FIG. 2A *(PRIOR ART)*
FIG. 2C *(PRIOR ART)*

AMINO-ACYL-TYPE AND CATECHOLAMINE-TYPE CONTRAST AGENTS FOR MRI

RELATED APPLICATIONS

This application is a continuation of application Ser. No. 08/169,301 filed Dec. 17, 1993 U.S. Pat. No. 5,562,894 which is a continuation-in-part of U.S. Ser. No. 08/086,349, filed Jun. 30, 1993 (abandoned); which is a contuation-in-part of U.S. Ser. No. 07/927,172, filed Aug. 7, 1992 (abandoned); which is a contuation-in-part of U.S. Ser. No. 07/744,470, filed Aug. 12, 1991 (abandoned); which is a contuation-in-part of U.S. Ser. No. 07/743,143, filed Aug. 9, 1991 (abandoned).

BACKGROUND OF THE INVENTION

1. Field of the Invention

The present invention relates to the preparation and use of amino-acyl-type and catecholamine-type hepatobiliary and cardiac contrast agents useful in magnetic resonance imaging. The contrast agents have multiple carboxyl groups to chelate a variety of metal (II) or (III) ions.

2. Description of Related Art

This invention relates to contrast agents for medical magnetic resonance imaging (MRI).

A contrast agent is an exogenous substance that either augments or suppresses the normal in vivo MRI signal, thereby yielding additional diagnostic information. The theory and applications of various types of contrast agents have been described in the literature (1,2). [The Arabic numbers in parentheses in this section refer to the articles cited in this section.]

The applications of a given MRI contrast agent are determined by its distribution in vivo. The mechanisms controlling the initial biodistribution can be classed as physico-chemical, i.e., dependent only upon such properties as molecular size, charge, lipophilicity, surface properties, etc.; or receptor-mediated, i.e., dependent upon the binding of a substrate to a specific receptor in or on cells. Different organs may handle the same contrast agent by different mechanisms. For example, the molecular size of the agent may result in its filtration by the kidneys (or confinement to the vascular space) while it is cleared by receptor-mediated transport in the liver.

Contrast agents exhibiting a physico-chemical distribution mechanism include the gadolinium (III) complex of diethylenetriaminepentaacetic acid (Gd-DTPA), which distributes in blood plasma and extracellular fluid, and albumin-(Gd-DTPA)$_n$, which remains largely intravascular (1,2). The former is used to demonstrate blood-brain barrier lesions or to reveal renal anatomy and function (3), while the latter has been used experimentally to delineate the vasculature (4) and determine brain blood volume (5,6). Iron-dextran, although a colloid, has a sufficiently long plasma half-life (12 hr) to be used as an intravascular T2 contrast agent (7), as do some superparamagnetic iron oxide particle preparations (8,9).

Because of its role in the removal of exogenous compounds from general circulation, the liver is able to actively take up and concentrate soluble, as well as particulate, contrast agents. The pathways followed by solutes from plasma to bile have been reviewed (10–11) and are diagrammed in FIG. 4. Passage into the hepatocyte across the cell membrane can take place by pinocytosis, passive diffusion, and/or by carrier-mediated systems that transport bile acids, bilirubin, organic anions, organic cations, neutral organic compounds, or inorganic ions. The substrate specificity of different carrier systems can partially overlap (e.g., organic anions and bile acids). The substrate may be metabolized intracellularly and/or conjugated with glucuronic acid or glutathione, for example. Finally, excretion into bile canaliculi again involves passage through a cell membrane. The mechanism of biliary excretion for a given compound may differ from that operative for its uptake.

The relative rates of metabolism, biliary elimination, and renal excretion determine the clearance of drugs and their metabolites from blood plasma and their persistence in any one organ system. However, presently the factors that direct one compound to be excreted in the bile and another in the urine are not completely understood. Molecular weight, polarity, and molecular structure in relation to binding to plasma and transporter proteins are important. There appears to be a general molecular weight threshold, which is species-dependent (ca. 300 for rats and 600 for humans) below which urinary excretion dominates (10–11). Hydrophilic-lipophilic balance appears to play a critical role in biliary excretion (10–11). However, a priori prediction is not presently possible.

The liver has provided the first example of receptor-mediated localization of an MR contrast agent—Fe-EHPG (EHPG is Ethylene-bis(hydroxyphenylglycine)) (12). Other iron (13–15), manganese (16–17), and gadolinium (18) chelates have since been described that have either potential for, or have demonstrated receptor-mediated hepatocyte uptake.

It has been reported by others that the anionic chelates Fe-EHPG, Fe-HBED (HBED=bis-(hydroxybenzyl) ethylenediaminediacetic acid), and Fe-PGDF (PGDF=N-3-(phenylglutaryl) desferrioxamine B) are transported in the liver by a system or systems inhibitable by BSP (bromosulfophthalein) (13,15).

The lipophilic chelate Gd-BOPTA ("benzyloxypropionictetraacetate," a derivative of DTPA) was shown to have significant biliary excretion (38.6% of injected dose in bile at 6 hr) (18). No information was reported on the mechanism of transport (e.g., passive diffusion or anionic transport) of this compound. Gd-BOPTA produced a larger signal enhancement (48%) in liver than Gd-DTPA (16%) in T1-weighted spin-echo images at 0.5 Tesla.

Additionally, other organs and tissues may possess receptors with affinity for certain classes of substrates, e.g., amino acids, peptides or catechol amines (19–24). These receptors may also bind molecules that resemble the substrate, e.g., a derivative of an amino acid that is present in a peptide substrate (22) or an amide derivative of a naturally occurring catechol amine such as dopamine. The contrast agents of this invention may in part localize by such a mechanism. Furthermore, the localization of the catechol containing contrast agent of the present invention may depend in part on their respective reduction-oxidation properties.

To date, magnetic resonance imaging (MRI) has played a minor role in imaging of the liver and abdomen of a human being because of degradation of image quality by motion artifacts, and by the lack of suitable contrast agents. Recent technical advances in instrumentation (e.g., self-shielded gradient coils) and pulse sequences (e.g., echo-planar and turbo-flash techniques) promise to alleviate the motion-related problems of the torso and abdomen, and make contrast agent development all the more important for continued progress in abdominal MRI.

General background in the use of MRI contrast agents and of their preparation and purification are described, for example, in:

H. Gries et al., U.S. Pat. No. 4,647,447;

R. B. Lauffer et al., U.S. Pat. No. 4,899,755 and 4,880,008;

B. L. Engelstad et al., U.S. Pat. No. 4,909,257;

D. L. White et al., U.S. Pat. No. 4,999,445.

1. R. B. Lauffer, "Paramagnetic metal complexes as water proton relaxation agents for NMR imaging: Theory and Design," *Chem. Rev.* (1987); 87:901–927.

2. S. M. Rocklage, et al. "Contrast Agents in Magnetic Resonance Imaging." Chapter 14, in *Magnetic Resonance Imaging*, 2nd ed., Stark D. D., Bradley W. G., eds. St. Louis: C. V. Mosby Co. (1992).

3. G. Bydder, "Clinical applications of Gadolinium-DTPA." in *Magnetic Resonance Imaging*. Stark D. D., Bradley W. G., eds. St. Louis: C. V. Mosby Co. (1988); 182–200 (Chap. 10).

4. M. E. Moseley et al., "Vascular mapping using Albumin-(Gd-DTPA), an intravascular MR contrast agent, and projection MR imaging," *J. Computer Assist Tomography* (1988); 13:219–221.

5. T. A. Kent et al., "Cerebral blood volume in a rat model of cerebral ischemia by MR imaging at 4.7 T,"*AJNR* (1989); 10:335–358.

6. D. L. White et al., "Determination of perfused cerebral blood volume using an intravascular MR contrast agent," *Book of Abstracts*: Society of Magnetic Resonance in Medicine (1989); 2:806.

7D. L. White et al., "Iron-Dextran as a magnetic susceptibility contrast agent: Flow-related contrast effects in the T2-weighted spin-echo MRI of normal rat and cat brain," *Magn.Reson.Med.* (1992); 24:14–28.

8. D. L. White et al., "Plasma clearance of ferrosomes, a long-lived superparamagnetic MRI contrast agent." *Book of Abstracts*: Society of Magnetic Resonance in Medicine (1990); 1:51.

9. R. Weissleder et al., "Ultrasmall superparamagnetic iron oxide: Characterization of a new class of contrast agent for MR imaging," *Radiology* (1990); 175:489–493.

10. L. S. Schanker, "Secretion of organic compounds into bile." in *The Handbook of Physiology. Alimentary Canal V*. Washington, D.C.: American Physiol. Society, Chap. 114:2433–2449.

11. C. D. Klaassen et al., "Mechanisms of bile formation, hepatic uptake, and biliary excretion," *Pharm. Rev.* (1984); 36:1–67.

12. R. B. Lauffer et al., "Iron-EHPG as a hepatobiliary MR contrast agent: Initial imaging and biodistribution studies," *J. Computer Assist. Tomoaraph*, (1985); 9:431–438.

13. B. Hoener et al., "Evaluation of Fe-HBED and Fe-EHPG as magnetic resonance contrast agents for assessing hepatobiliary function," *J. Magn. Reson. Imaging*, (1991); 1:357–362.

14. K. A. Muetterties et al., "Ferrioxamine B derivatives as hepatobiliary contrast agents for magnetic resonance imaging," *Magn. Reson. Med.* (1991); Vol. 22, pp. 88 to 100.

15. B. Hoener et al., "Hepatic transport of the magnetic resonance imaging contrast agent Fe(III)-N-(3-Phenylglutaryl) desferrioxamine B," *Magn. Reson. Med.* (1990); 17:509–51.

16. D. L. White et al., "Clearance, excretion, and organ distribution of a new MRI contrast agent Manganese-Dipyridoxal-Diphosphate (Mn-DPDP)." *Abstract Book*: Society of Magnetic Resonance in Medicine (1988) 1:531.

17. S. W. Young, "MRI measurement of hepatocyte toxicity using the new MRI contrast agent manganese dipyridoxal diphosphate, a manganese/pyridoxal 5-phosphate chelate," *Mag. Reson. Med.* (1989); 10:1–13.

18. P. Pavone et al., "Comparison of Gd-BOPTA with Gd-DTPA in MRI imaging of rat liver," *Radiology* (1990); 176:61–64.

19. P. Ascher, "Glutamate receptors and glutamatergic synapses. In *Receptors. Membrane Transport and Signal Transduction*. A. E. Evangelopoulis et al., Berlin: Springer Verlag. (1989): 127–146.

20. F. P. Lehman, "Stereoselective Molecular Recognition in Biology. In *Receptors and Recopnition*, Vol. 5, Series A. Cuatrecasas P. and Greaves M. F. London: Chapman-Hall (1978).

21. R. D. O'Brien, ed. *The Receptors, A Comprehensive Treatise*, Vol. 1, New York: Plenum Press (1979).

22. S. S. Schiffman et al., "The Search for Receptor that Mediate Sweetness," In *The Receptors*, Vol. 4, Conn, P. M., ed. Academic Press. Orlando. (1986).

23. A. S. Horn, et al., eds. *The Neurobiology of Dopamine*. Academic Press. New York. 1979.

24. B. J. Clark. "The role of dopamine in the periphery," in *The Dopaminergic System*, B. Halasz, et al., eds., Springer-Verlag, Berlin, 1985, p 27–39.

All reference articles, patents, etc. cited in this application are incorporated herein by reference in their entirety.

It would be very useful to have organic chelate metal ion complexes which are specific for MRI imaging of the liver, the biliary tree, the upper small intestine, or the myocardial tissue. The present invention provides complexes and methods having these useful advantages.

SUMMARY OF THE INVENTION

In a first aspect, the present invention relates to an amino-acyl-type magnetic resonance imaging contrast agent, comprising the complex:

$$L^1 — M$$

wherein M is a metal (II) or (III) ion independently selected from the group consisting of metals of atomic number 21 to 31, metals of atomic number 39 to 50, the lanthanide metals having an atomic number from 57 to 71, and metals of atomic number 72 to 82; and $L^1$ is a polydentate amino-acyl-type chelating moiety of Formula 1:

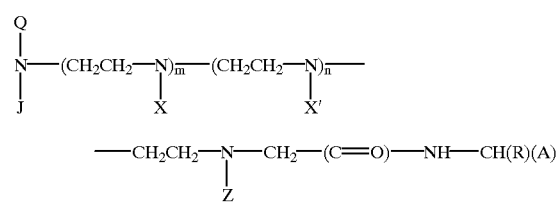

wherein Q, J, X, X' and Z are each independently selected from the group consisting of —$CH_2$—(C=O)$OR^1$ and —$CH_2$—(C=O)—NH—CH(R)(A);

wherein each R is independently selected from the group consisting of -hydrogen, —K, —W and —K—W, wherein each K is an alkyl group having 1–7 carbon atoms, and each W is independently selected from the group consisting of aryl, substituted aryl, heteroaryl and substituted heteroaryl; and each A is a carbonyl-containing moiety independently selected from the group consisting of —(C=O)OR$^1$ and —(C=O)—N(R$^2$)(R$^3$), wherein R$^1$, R$^2$ and R$^3$ are independently selected from the group consisting of hydrogen (i.e. the acid), alkyl having 1–7 carbon atoms, cyclohexyl, phenyl, benzyl, 1-naphthyl and 2-naphthyl, provided that when every A is —(C=O)OR$^1$ and every R$^1$ is hydrogen, then at least one R is —W or —K—W; and m is selected from 0, 1, 2 or 3, and n is selected from 0 or 1;

or the pharmaceutically acceptable salt(s) thereof.

Another aspect of this invention relates to a polydentate amino-acyl-type chelating compound (L$^1$) of Formula 1, supra.

Another aspect of this invention relates to a method of preparing a polydentate amino-acyl-type chelate compound (L$^1$) of Formula 1, which method comprises:

(a) contacting a structure of the following formula:

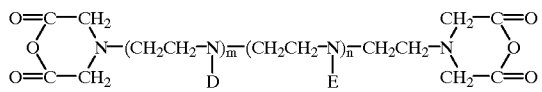

wherein D and E are CH$_2$(C=O)OR$^1$, with an amino acid of the structure H$_2$N—CH(R)—(C=O)OH, an ester of the structure H$_2$N—CH(R)—(C=O)OR$^1$ or an amide of the structure H$_2$N—CH(R)—(C=O)—N(R$^2$)(R$^3$);

wherein each R is independently selected from the group consisting of —K, —W and —K—W, wherein each K is an alkyl group having 1–7 carbon atoms, and each W is independently selected from the group consisting of aryl, substituted aryl, heteroaryl and substituted heteroaryl;

R$^1$, R$^2$ and R$^3$ are independently selected from the group consisting of hydrogen (i.e. the acid), alkyl having 1–7 carbon atoms, cyclohexyl, phenyl, benzyl, 1-naphthyl and 2-naphthyl, and m is selected from 0, 1, 2 or 3, and n is selected from 0 or 1, in an anhydrous dipolar aprotic solvent at between about 50 and 150°; and (b) removing the solvent and recovering the compound of Formula 1.

Another aspect of this invention relates to a method of examining a mammal in a diagnostic manner, which method comprises:

(a) injecting the mammal with an amino-acyl-type contrast agent in a dose amount having a concentration of the complex L$^1$—M of between about 0.5 and 5000 micromol/kg of body weight of the mammal;

(b) placing the mammal of step (a) in a magnetic field irradiating with radio-frequency energy such that nuclear magnetic resonance can be detected; and (c) analyzing the imaging nuclear magnetic resonance signals obtained.

In another aspect, the present invention relates to a catecholamine-type magnetic resonance imaging contrast agent, comprising the complex:

L$^2$—M wherein M is a metal (II) or (III) ion independently selected from the group consisting of metals of atomic number 21 to 31, metals of atomic number 39 to 50, the lanthanide metals having an atomic number from 57 to 71, and metals of atomic number 72 to 82; and L$^2$ is a polydentate catecholamine-type chelating moiety of Formula 2:

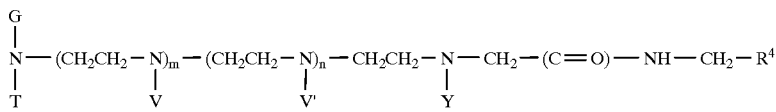

wherein G, T, V, V' and Y are each independently selected from the group consisting of —CH$_2$—(C=O)OR$^1$ and —CH$_2$—(C=O) —NH—CH$_2$—R$^4$;

wherein each R$^4$ is independently selected from the group consisting of —CH$_2$-aryl, —CH$_2$CH$_2$-aryl, —CH$_2$-(substituted aryl), and —CH$_2$CH$_2$-(substituted aryl); and m is selected from 0, 1, 2 or 3, and n is selected from 0 or 1;

or the pharmaceutically acceptable salt(s) thereof.

Another aspect of this invention relates to a polydentate catecholamine-type chelator (L$^2$) of Formula 2, supra.

Another aspect of this invention relates to a method of preparing a polydentate catecholamine-type chelator (L$^2$) of Formula 2, which method comprises:

(a) contacting a structure of the following formula:

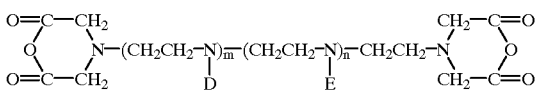

wherein D and E are CH$_2$(C=O)OR$^1$, with a derivative of the structure NH$_2$—CH$_2$—R$^4$; wherein R$^4$ is independently selected from the group consisting of —CH$_2$-aryl, —CH$_2$CH$_2$-aryl, —CH$_2$-(substituted aryl), and —CH$_2$CH$_2$-(substituted aryl); and m is selected from 0, 1, 2 or 3, and n is selected from 0 or 1, in an anhydrous dipolar aprotic solvent at between about 50 and 150°; and (b) removing the solvent and recovering the compound of Formula 2.

Another aspect of this invention relates to a method of examining a mammal in a diagnostic manner, which method comprises:

(a) injecting the mammal with a catecholamine-type contrast agent in a dose amount having a concentration of the complex L²—M of between about 0.5 and 5000 micromol/kg of body weight of the mammal;

(b) placing the mammal of step (a) in a magnetic field irradiating with radio-frequency energy such that nuclear magnetic resonance can be detected; and (c) analyzing the imaging nuclear magnetic resonance signals obtained.

These metal ion chelates produce T1 contrast effects in the heart, liver, biliary tree, and upper small intestine. They demonstrate function, as well as anatomy. These contrast agents have low toxicities, and unlike iron from superparamagnetic particulates, the metal from these compounds should be rapidly and relatively completely cleared from the body. Therefore, these contrast agents are of substantial significance to useful abdominal MRI.

BRIEF DESCRIPTION OF THE FIGURES

FIGS. 1A, 1B, 1C and 1D are each a representation of the structures of the compounds BOPTA, BSP, DPDP and DTPA, respectively.

FIGS. 2A, 2B, 2C and 2D are each a representation of the structures of the chelates EDTA, EDTP, EHPG and HBED, respectively.

Figure 3:
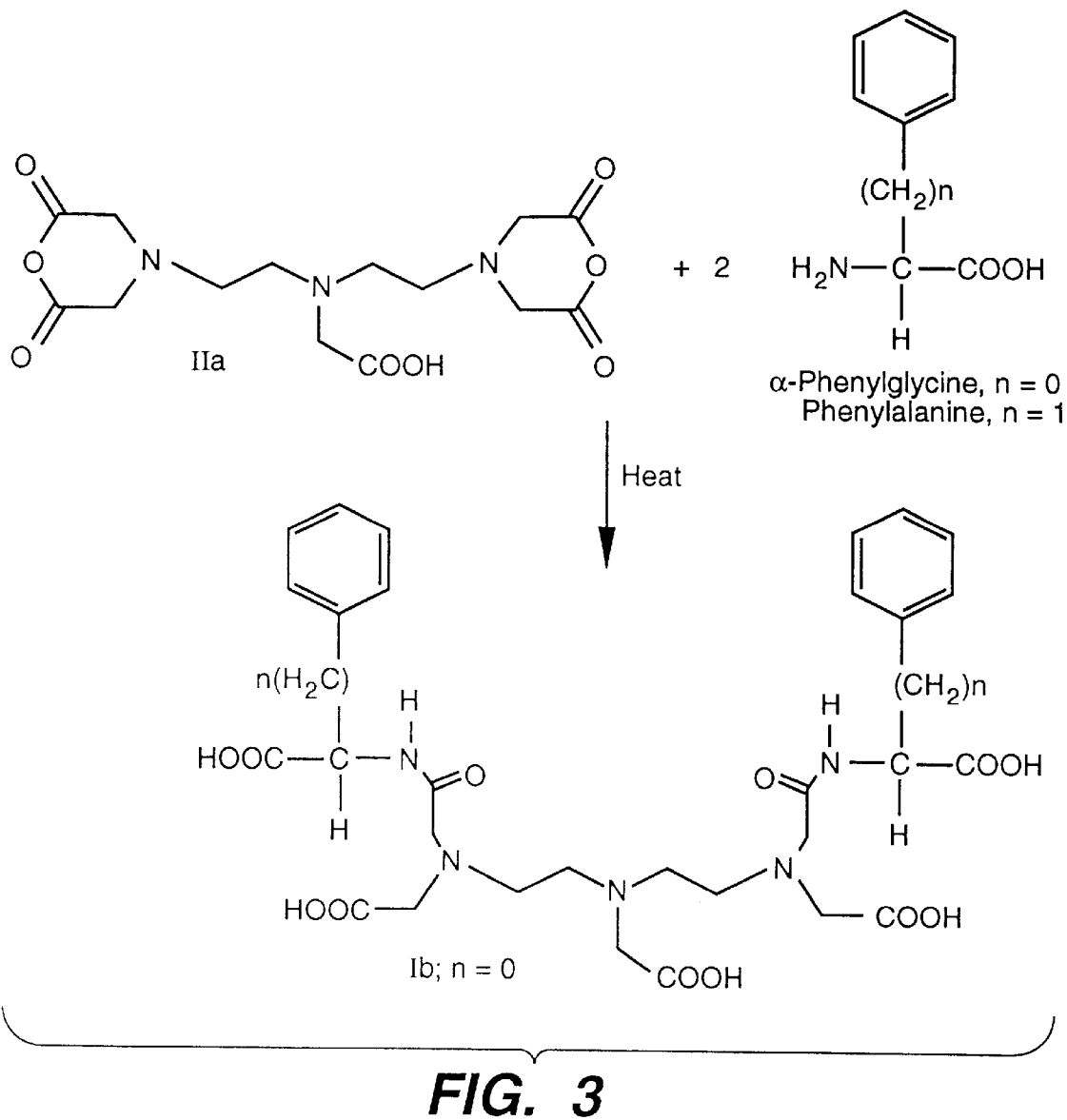
FIG. 3 is a representation of a species of the general reaction to produce a bis amino acid substituted chelate.
Figure 4:
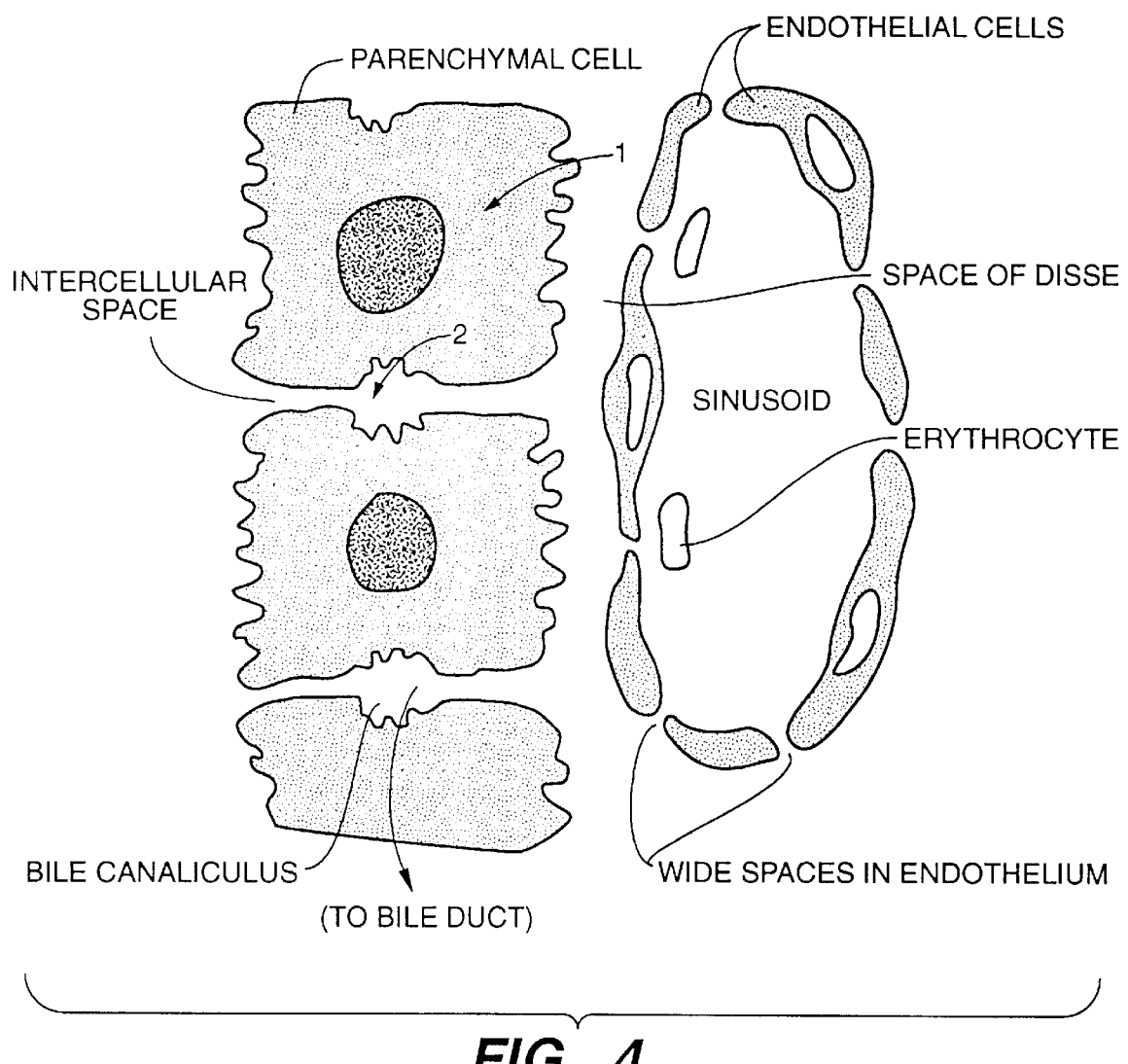
FIG. 4 is a cross-sectional representation of the cells, components and pathways found in the hepatobiliary region.

On FIGS. 9 to 13 and 16 to 20 solid vertical lines within the graph are shown ending in a horizontal line. The center box of this vertical line is the average for the observation at that point. The horizontal lines at either end of the vertical line are located at one standard derivation from the center value.

DETAILED DESCRIPTION OF THE INVENTION AND PREFERRED EMBODIMENTS

Definitions

As used herein:

"Alkylene" refers to methylene, ethylene, propylene, and the like up to seven carbon units. This usage is equally applicable to moieties comprising alkylene groups such as the alkyl, haloalkyl and alkoxyl moieties of the present invention.

"Amino acid" refers generally to the type of α-amino acids found in living subjects or mammals. However, synthetic α-amino acids which are not found in nature are also useful. Further these D- and L- amino acids as separate chiral isomers are independently useful. Mixtures of the D- and L- isomers are also contemplated in this invention. A variety of such amino acids and their derivatives are well known in the art; see, e.g., *Beilsteins Handbuch der Orcianischen Chemie* (Springer Verlag, Berlin) and *Chemical Abstracts* which provide references to publications describing the properties and preparation of such compounds.

"Metal of atomic number 21 to 31" refers to scandium, titanium, vanadium, chromium, manganese, iron, cobalt, nickel, copper, zinc and gallium respectively. Paramagnetic ions are especially preferred. Iron, manganese, nickel, chromium, cobalt are preferred.

"Metal (lanthanides) having an atomic number from 57 to 71" refers to lanthanide, cerium, praseodymium etc. to lutetium, respectively. Paramagnetic gadolinium (III) or dysprosium (III) are preferred.

"Substituted aryl" and "substituted heteroaryl" refer to moieties containing aromatic rings having one or more ring substituents, typically 1–3 ring substituents, that are independently selected from relatively non-reactive (and relatively non-toxic) groups such as alkyl having 1–7 carbon atoms, halo, haloalkyl having 1–7 carbon atoms, hydroxyl, carboxyl, acetoxyl, alkoxyl having 1–7 carbon atoms, amino, nitro, nitroso, sulfonyl and thio; and not from relatively reactive groups such as isothiocyanate (—N=C=S) and the like.

As is common, formulas are sometimes written on a single line with substituents of an atom listed (in parentheses) after the atom to which they are attached. Thus, for example, the formula:

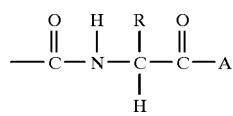

may be represented as —(C=O)—NH—CH(R)—(C=O)—(A). Other abbreviations used herein include, for example, —(L-PheOEt)$_2$ for -bis(L-phenylalanine ethyl ester).

The contrast agents of this invention localize in several organ systems, e.g., in the kidney, urinary tract, and urinary bladder; in the liver, biliary tree, and intestinal lumen; and in the myocardium. This localization results in increased MRI signal and image contrast. The resulting images show both improved anatomic detail and allow the functional state of certain organ systems, e.g., the urinary and biliary systems, to be ascertained.

This localization probably involves a combination of physico-chemical and receptor-based mechanisms. For example, binding to blood components results in enhancement of the blood pool and may contribute to heart enhancement. Localization in the liver may result from recognition and transport by hepatocytes. Other mechanisms may also be involved. It may be possible to target other organs and tissues by selective modification of the structure of the metal chelate contrast agent.

A. AMINO-ACYL-TYPE CONTRAST AGENTS (L$^1$—M)
Preparation of Amino-Acyl-Type Chelating Structures (L$^1$)

In one embodiment the present invention relates to polydentate amino-acyl-type chelating structures (L$^1$) of Formula 1, supra, wherein A is a carbonyl-containing moiety which is an acid or ester (i.e. A is —(C=O)OR$^1$, and R$^1$ is independently selected from the group consisting of hydrogen (i.e. the acid), alkyl having 1–7 carbon atoms, cyclohexyl, phenyl, benzyl, 1-naphthyl and 2-naphthyl).

The following is a general description of the synthesis of such chelating ligands. Specific descriptions are found in the Experimental Section.

In the synthesis of the compounds of Formula 1, the precursor can be DTPA-bis(anhydride) (or a similar structure, e.g. EDTA-bis(anhydride)) which can be contacted with an amino acid of the structure of the known natural or synthetic amino acids, e.g. D, L, or mixtures thereof. Thus, the —CH$_2$—(C=O)—NH—CH(R)(A) moieties may contain a chiral carbon atom (i.e. the C in —CH(R)(A)) which is a chiral center of the D or L configuration and, when the contrast agent comprises a multitude of such moieties, the multitude of chiral centers may be either of the D or the L configuration or a mixture thereof. Generally, only single amino acid residues are incorporated as the amino-acyl-type moieties (i.e. —NH—CH(R)(A)) in Formula 1; that is, polypeptide bonds are usually not formed.

The chelating structures of the present invention can be prepared using a variety of natural and synthetic amino acids and their derivatives that can be incorporated as the —NH—CH(R)(A) moiety. Such amino acids and their derivatives are well known in the art; see, e.g., *Beilsteins Handbuch der Organischen Chemie* (Springer Verlag, Berlin) and *Chemical Abstracts* which provide references to publications describing the properties and preparation of such compounds, which publications are incorporated herein by reference. Examples of substituted α-amino acids that can be covalently linked to, e.g., DTPA-bis(anhydride) via their free amino groups include esters and amides of amino acids as well as their derivatives. Preferred α-amino acids for use in the present invention are phenylglycine, phenylalanine, tryptophan, tyrosine and histidine, and substituted derivatives thereof. Preferred substitutions on the aromatic rings of these amino acids include alkyl having 1–7 carbon atoms, halo, haloalkyl having 1–7 carbon atoms, hydroxyl, carboxyl, acetoxyl, alkoxyl having 1–7 carbon atoms, amino, nitro, nitroso, sulfonyl and thio. Presently, 4-t-butylphenylalanine and p-ethoxyphenylalanine are especially preferred amino acid derivatives for use in the present invention.

References describing the properties and preparation of such amino acid derivatives can be found in numerous published sources including *Beilsteins Handbuch* and *Chemical Abstracts*, supra. In *Beilsteins Handbuch*, for example, references describing the properties and preparation of phenylalanine, phenylglycine and tyrosine derivatives can be found in Volume 14 of the Hauptwerke (Main Series), and Volume 14 of the Erganzungwerke (Supplementary series). References describing the properties and preparation of tryptophan derivatives can be found in Volume 22 of the Hauptwerke and Volume 22 of the Erganzungwerke. Various methods of synthesizing amino acids and their derivatives are also described in *Synthesis of Amino Acids*, G. C. Barrett, Chapter 8 in "Chemistry and Biochemistry of the Amino Acids" by G. C. Barrett (ed.) (Chapman and Hall, London, 1985). A number of amino acid derivatives are also readily available from commercial suppliers such Aldrich Chemical Co. and Fluka Chemical Co.

With the bis(anhydride), if a limited amount (e.g. 0.5 equivalent) of the amino acid is used, production of the mono amino acid derivative is favored. If two equivalents of amino acid is used, then the bis-amino acid derivative is produced. For DTPA or higher analogs of polycarboxylic acids, forcing conditions, such as using a coupling reagent and a large excess of the amino acid or protected amino acid may be required.

Any anhydrous dipolar aprotic solvent can be used for the synthesis. Dimethylformamide (DMF), dimethylacetamide, acetonitrile or the like are useful. DMF is preferred. The reaction mixture is heated at 70 to 100° C. for between about 2–12 hr, preferably between 90 and 100° C. for 4–5 hr, especially 6 hr.

The reaction mixture is cooled and the solvent is removed using a conventional rotary evaporator or its equivalent. In one aspect, the present invention relates to a novel preparation of the compounds of Formula 1.

In another embodiment the present invention relates to polydentate amino-acyl-type chelating structures (L$^1$) of Formula 1, supra, wherein A is a carbonyl-containing moiety which is an amide (i.e. A is —(C=O)—N(R$^2$)(R$^3$) wherein R$^2$ and R$^3$ are each independently selected from the same group defined for R$^1$, supra).

The amides and related structures (free amide, monosubstituted amide or disubstituted amide) are produced by starting with the appropriate amino acid amide (usually as the hydrochloride). Some purification of the amino acid may be needed.

The amino acid amide is then contacted with the corresponding dianhydride as is described above for the amino acid ester. If a less-than-equivalent amount of amino acid amide is used and at high dilution in the solvent the mono amino acid amide is favored. If a stoichiometric excess of the amino acid amide is used, the diamine acid amide structure is obtained.

The amide structures are also described in Examples 12 to 22. The amide structures are useful in MRI, because they have good contrast properties for specific tissue and have a longer useful half-life in a mammalian system.

Preparation of the metal ion chelate complex (L¹—M)

The general description of the preparation of chelate metal ion complexes is conventional in the art; see, e.g., the references cited above.

Metal chelates are typically prepared by the reaction of a metal salt or oxide with the chelating ligand in a suitable aqueous or organic solvent in the appropriate stoichiometric ratio. Elevated temperatures are sometimes required. The pH of the reaction mixture is then adjusted with a base to obtain the corresponding chelate salt. Alternatively, acid can often be used to obtain the protonated chelate.

Preferably, in the amino-acyl-type contrast agents, at least one R or R¹ group of the ligand (L¹) comprises an aromatic or heteroaromatic moiety.

The R group preferred is independently selected from —W and —K—W, wherein K is an alkyl group having 1–7 carbon atoms, and W is independently selected from the group consisting of aryl, substituted aryl, heteroaryl and substituted heteroaryl; provided further that, if W is substituted aryl or substituted heteroaryl, then the aromatic ring substituents are independently selected from relatively nonreactive (and relatively non-toxic) groups such as alkyl having 1–7 carbon atoms, halo, haloalkyl having 1–7 carbon atoms, hydroxyl, carboxyl, acetoxyl, alkoxyl having 1–7 carbon atoms, amino, nitro, nitroso, sulfonyl and thio; and not from relatively reactive groups such as isothiocyanate (—N=C=S) and the like. The K group preferred is selected from the group consisting of methylene, ethylene and propylene.

The more preferred R group is independently selected from the —K—W moieties shown below:

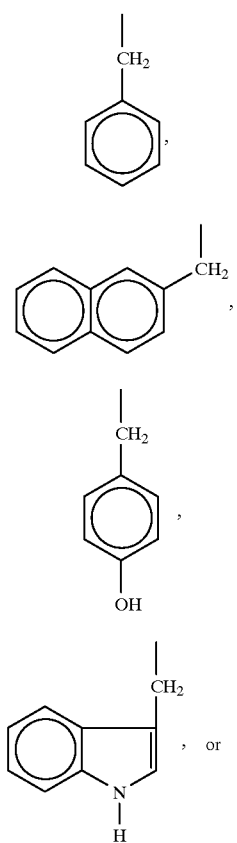

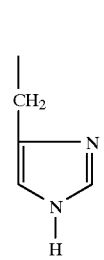

and their derivatives substituted with 1 to 3 groups independently selected from alkyl having 1–7 carbon atoms, halo, haloalkyl having 1–7 carbon atoms, hydroxyl, carboxyl, acetoxyl, alkoxyl having 1–7 carbon atoms, amino, nitro, nitroso, sulfonyl and thio.

Presently, the most preferred R group is —K—W wherein W is selected from the group consisting of hydroxyphenyl, methoxyphenyl, ethoxyphenyl and t-butylphenyl; most preferably p-ethoxyphenyl and p-t-butylphenyl.

Each $R^1$, $R^2$ and $R^3$, when present, is independently selected from the group consisting of H (i.e. the acid), alkyl having from 1–7 carbon atoms (i.e. the mono, di, tri, etc., acid ester), and cyclic groups such as cyclohexyl, phenyl, benzyl, 1-naphthyl and 2-naphthyl.

Preferred metal ions (M) are gadolinium (III), dysprosium (III), chromium (III), iron (II), iron (III), cobalt (III), manganese (II) and manganese (III). Paramagnetic metal ions are preferred. Especially preferred are gadolinium (III) and dysprosium (III).

Presently preferred amino-acyl-type contrast agents of this invention are gadolinium(4-t-butylphenylalanine-DTPA) and gadolinium(p-ethoxyphenylalanine-DTPA).

B. CATECHOLAMINE-TYPE CONTRAST AGENTS (L²—M)

In another aspect the present invention relates to catecholamine-type chelating structures (L²), and metal ion complexes thereof (L²—M), comprising one or more —NH—CH₂—R⁴ moieties (wherein each $R^4$ is independently selected from the group consisting of —CH₂-aryl, —CH₂CH₂-aryl, —CH₂-(substituted aryl), and —CH₂CH₂-(substituted aryl)).

When a catecholamine-type compound having a —NH—CH₂—R⁴ moiety is contacted with the bisanhydride as described for the corresponding amino acid ester or amide, the expected compound is obtained. When the substituents on the aryl group are hydroxyl, aqueous base should be avoided.

In preferred embodiments of this type, the present invention concerns the preparation of a chelating ligand that bears one or more catecholamine groups, making a stable chelate of this ligand with a useful metal ion, and using the chelate for diagnostic imaging or spectroscopy.

In preferred catecholamine-type compounds, $R^4$ is a substituted aryl which is selected from substituted phenyl and substituted naphthyl, and substituted aryl is substituted with 1 to 3 groups independently selected from the group consisting of hydroxyl, alkyl having 1–7 carbon atoms, alkoxyl having 1–7 carbon atoms, halo, haloalkyl, nitro, nitroso, and amino.

In more preferred catecholamine-type compounds, $R^4$ is a substituted phenyl which is substituted with two groups selected from hydroxyl, methoxyl and ethoxyl.

If the metal ion is paramagnetic, e.g., Gd(III) or Dy(III), the chelate can produce contrast enhancement in an MRI, or cause shifts, broadening, or other changes in a magnetic resonance spectrum.

These novel agents constitute an improvement over the prior art in that they tend to be localized in certain types of tissue by virtue of their resemblance to naturally occurring catecholamines and/or their redox and other physicochemical properties. Two derivatives of dopamine (also 3-hydroxytyramine or "3-HTA"), namely DTPA-bis(3-hydroxytyramide) and DTPA-bis(3,4-dimethoxyphenethylamide) are particularly useful. These ligands were reacted with Gd(III) to produce the chelates, Gd-DTPA-(3-HTA)$_2$ and Gd-DTPA-(3,4-DMPE)$_2$, respectively. These were used as contrast agents in the MRI of rats as described in the Examples. Both chelates demonstrated useful enhancement of heart, lungs, kidney and liver. However, the former selectively enhanced the heart.e
Determining the Efficacy of Contrast Arents of the Present Invention MRI contrast agents have magnetic properties capable of altering image intensity. The activity of the compounds of the present invention can be examined directly by imaging in rodents, as is described below. However, it is also possible to obtain an initial estimate of the magnetic efficacy in vitro by comparing, for example, the water proton relaxivity or the magnetic susceptibility of a compound relative to known contrast agents.

Suitable MRI contrast agents will also localize for a time in the target compartment, tissue or organ. Radio-labeled analogs can be used to quantify tissue concentrations. Such techniques have been described in the art; see, e.g., K. A. Muetterties et al., "Ferrioxamine derivatives as hepatobiliary contrast agents for magnetic resonance imaging," *Magn. Reson. Med.* (1991), Vol. 22, pp. 88 to 100.

Hepatic uptake, for example, is generally reflected in increased biliary excretion and fecal elimination. Thus, hepatic uptake can be estimated by determining the relative amounts of urinary and biliary excretion (see, e.g., Example 22, below); or by determining the relative amounts of urinary and fecal excretion (see, e.g., Example 23, below).

Finally, as described below, imaging studies in laboratory animals such as rats, can also be used to examine the pharmacokinetics and biodistribution of a particular contrast agent.
Magnetic Resonance Imaging In vivo magnetic resonance imaging of organs and tissue in both laboratory animals and humans is now conventional and well established.

Figure 5A:
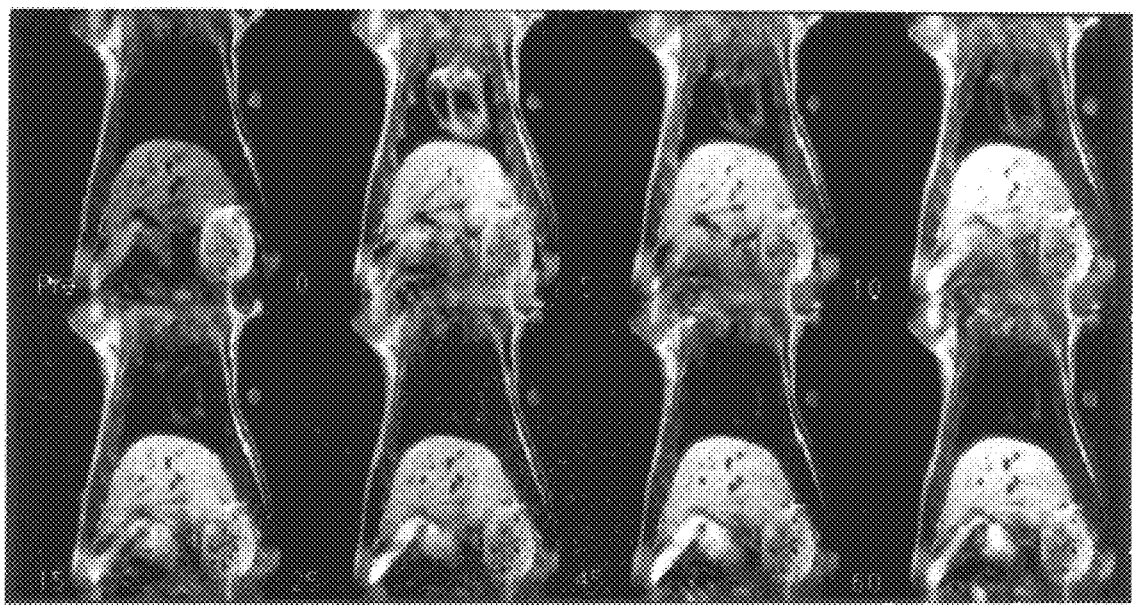
FIG. 5A is a photograph of T1-weighted magnetic resonance images of a rat at various times (indicated in minutes) after injection of the Gd-DTPA-bis(phenylalanine). Approximately 0.1 mmol/kg dose.
Figure 5B:
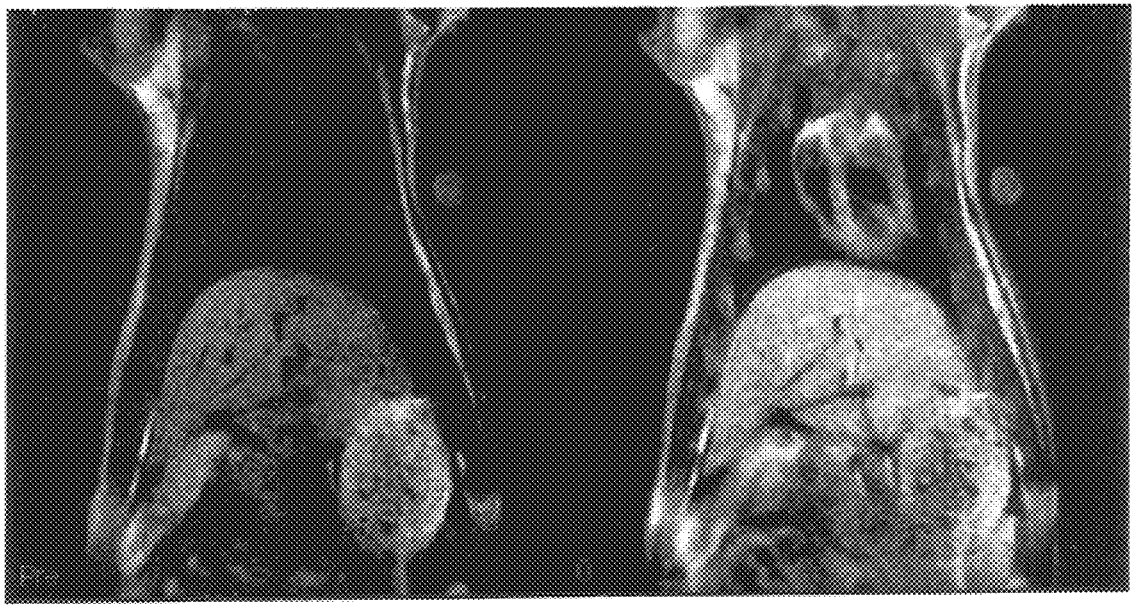
FIGS. 5B and 6B are photographic enlargements of the pre- and 0-min post injection images of FIG. 5A and 6A, respectively.

FIG. 5 is a photograph of T1-weighted magnetic resonance images of a rat obtained before, and at 0, 5, 10, 15, 25, 45 and 60 minutes after the injection of Gd-DTPA-bis (phenylalanine) at a dose of mmol/kg body weight. The images are 60 mm×60 mm×3 mm thick slices in the coronal plane. The region covered extends from just above the heart to somewhat below the liver. Enlargements of the pre- and 0-min post images are shown in FIG. 5B. Imaging parameters are indicated along the left of the Figure and include the repetition time (3000000 microseconds), echo time (6000 microseconds), number of signal averages (4), and the image matrix size (128×256). The increase in signal intensity, particularly in the heart and liver, are readily apparent. Increase in signal intensity of the intestinal lumen is particularly apparent in the 25 min and later images, and suggests that contrast agent has been excreted into that organ.

Figure 6A:
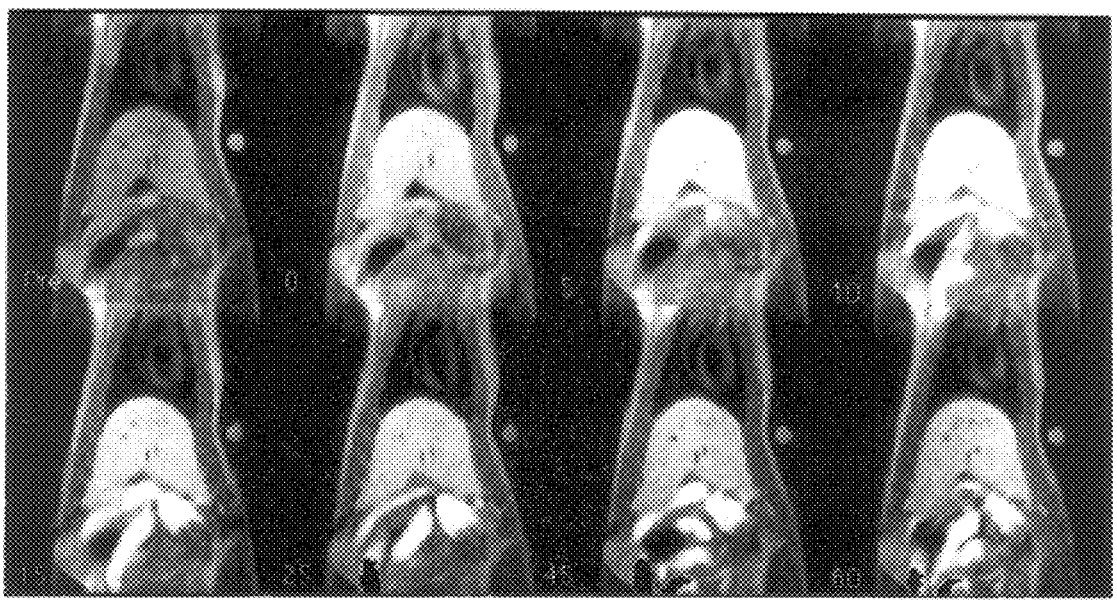
FIG. 6A is a photograph of T1-weighted magnetic resonance images at various times (indicated in min) obtained as in FIG. 5A and FIG. 5B for the Gd-DTPA-bis(phenylalanine ethyl ester).
Figure 6B:

FIGS. 6A and 6B are photographs of T1-weighted magnetic resonance images obtained as described in FIG. 5A and 5B, except that Gd-DTPA-bis(phenylalanine ethyl ester) was used as the contrast agent. Note that this compound results in different apparent enhancement in the liver and heart as compared to that shown in FIG. 5A and 5B. These results suggest that the two compounds have significantly different biodistributions and pharmacokinetics.

Specific experiments are described in detail below in the Examples.
Administration of Contrast Agent Any physician can determine the best mode of administration of the contrast agent. Generally, injection into a vein is used.

Suitable pharmaceutical compositions comprising the contrast agents of the present invention may include, for example, various buffers and/or stabilizers, as is well-known in the art; see, e.g., *Remington's Pharmaceutical Sciences*, Mack Publishing Company, latest edition, Easton, Pa.

The contrast agents described herein are useful for the magnetic resonance imaging of the heart, liver, biliary tree, bladder and intestine of a subject, e.g., an animal, a mammal, especially a human being.

The following examples are provided to illustrate the invention—not to limit it.

EXAMPLE 1

PREPARATION OF DTPA-BIS (PHENYLGLYCINE)

In a 50-mL round-bottom flask equipped with a magnetic stirrer and a reflux condenser, and heated by an oil bath, was placed 1.10 g (3.08 mmol) of DTPA-bis(anhydride) (Aldrich Chemical Co.), 0.93 g (6.15 mmol) of d,l-α-phenylglycine (Fluka Chemical Co.), and 24 mL of dry dimethylformamide (Aldrich Chemical Co.). The reaction mixture was heated to 90–100° C., and held within that temperature range for 6 hr. It was then allowed to cool to room temperature, and the solvent was removed using a rotary evaporator. The residue was washed by trituration with ether to yield 2 g of white solid of structure Ib (FIG. 3).

EXAMPLE 2

PREPARATION OF THE Gd(III) COMPLEXES OF DTPA-BIS(PHENYLGLYCINE)

A solution of 2 mg (30 $\mu$mol) of DTPA-bis(phenylglycine) of Example 1 in 1 mL of water was treated with 14 mg (38 $\mu$mol) of GdCl$_3$.6H$_2$O. The pH of the resulting mixture was adjusted to 7.0 by addition of dilute sodium hydroxide solution. Insoluble Gd(OH)$_3$ was removed from the reaction mixture by filtration through a 0.22$\mu$ filter. The T1 relaxation time of the resulting solution (1.3 mL volume) was 7 millisecond (ms) at 0.25 Tesla and 37° C.

EXAMPLE 3

MAGNETIC RESONANCE IMAGING OF A RAT USING Gd-DTPA-BIS(PHENYLGLYCINE)

A 300 g male Sprague-Dawley rat was anesthetized with an intraperitoneal injection of a mixture of ketamine and diazepam, and a catheter was inserted into a lateral tail vein. The rat then was placed in a 5-cm inside diameter (i.d.) imaging coil in the bore of a 2-Tesla imager-spectrometer system (GE CSI; General Electric Co., Fremont, Calif.). A T1-weighted spin-echo image of the animal's abdomen in the coronal plane was then obtained (TR 315 ms; Te 15 ms; 128×256 image matrix; NEX=4; 3 mm slice thickness). Next, 1.0 g of the Gd-DTPA-bis(phenylglycine) solution described in Example 2 was injected via the catheter. A series of post-injection images were obtained. The images displayed an initial small enhancement in the liver. As this enhancement decreased with time, increased intensity in the rat's small intestine then was observed, indicating hepatobiliary transport of the contrast agent. Intensity data are summarized below.

TABLE 1

IMAGE REGION-OF-INTEREST % ENHANCEMENT

| Time | Liver | Small Intestine | Muscle |
|---|---|---|---|
| (min post-injection) | | | |
| 0–3 | 4 | 14 | 19 |
| 15–18 | 7 | 42 | 2 |
| 30–33 | 2 | 32 | 6 |

EXAMPLE 4

PREPARATION OF DTPA-BIS(L-PHENYLALANINE ETHYL ESTER)

L-phenylalanine ethyl ester hydrochloride, 4.6 g (20 mmol; Sigma Chemical Co., St. Louis, Mo.), was dissolved in 15 mL of water and treated with 35 mL of saturated sodium bicarbonate solution. The resulting solution was extracted with four 10 mL portions of methylene chloride, and the organic extract was dried over anhydrous magnesium sulfate. The dried methylene chloride solution then was filtered to remove remaining drying agent, and the filtrate was concentrated to an oil using a rotary flash evaporator. This residue was further dried under high vacuum for several hours to yield 3.75 g of free base.

DTPA-bis(anhydride), 2.85 g (8.0 mmol), 10 mL of dimethylformamide (DMF), and 4.2 mL (24 mmol) of diisopropylethylamine (DIPEA) (Sigma Chemical Co., St. Louis, Mo.) were combined in a 50 mL round-bottom flask equipped with a magnetic stirrer. The phenylalanine described above was dissolved in 10 mL of DMF, and the resulting solution added via syringe to the flask. The reaction mixture was warmed to 40° C., and then stirred for 13 hr at ambient temperature without external heating.

At the end of the 12 hr period, the reaction mixture was concentrated in vacuo to yield a viscous residue. This material was triturated with 100 mL of acetone, and the volatile components of the resulting mixture were removed in vacuo. The solid residue was recrystallized from a mixture of 125 mL of 60/40 water/ethanol. The white, crystalline product was washed with two 25-mL portions of cold ethanol, and the washed solid was dried in vacuo at 40° C. for 1 hr to obtain 3.0 g (50% of theory).

Analytically pure product was obtained by dissolving 1 g of the above crystals in 75 mL of ethanol at 80–85° C., treating the resulting solution with decolorizing charcoal, removing the latter by filtration, and cooling the filtrate in an ice bath. Seed crystals were then added, and after 45 min, 0.6 g of recrystallized solid was isolated by filtration.

Anal: Calcd. for $C_{36}H_{49}N_5O_{12}$: C, 58.13; H, 6.64; and N, 9.42. Found: C, 57.75; H, 6.57; and N, 9.36.

EXAMPLE 5

PREPARATION OF DTPA-BIS(1-PHENYLALANINE BENZYL ESTER)

DTPA-bis(phenylalanine benzyl ester) was similarly prepared (according to Example 4) from L-phenylalanine benzyl ester p-toluene-sulfonic acid salt, 4.28 g (10 mmol; Sigma Chemical Co., St. Louis, Mo.). Ethyl acetate was used in place of ethanol for crystallization. The yield was 2.6 g (75% of theory).

EXAMPLE 6

PREPARATION OF DTPA-BIS(L-PHENYLALANINE)

A solution of 1.23 g (1.42 mmol) of DTPA-bis (phenylalanine benzyl ester) in 15 mL of methanol was combined with 0.1 g Pd/carbon catalyst (Aldrich Chemical Co., Milwaukee, Wis.) in a 25-mL round-bottom flask. This mixture was treated with hydrogen gas at one atmosphere pressure for 6 hr. The reaction mixture was then filtered through a bed of diatomaceous earth filter aid. Volatile components were removed from the filtrate in vacuo. The yield was 0.94 g (97% of theory) of product, a somewhat hygroscopic white solid.

Anal: Calc'd. for $C_{32}H_{31}N_5O_{12} \cdot 2H_2O$: C, 53.10; H, 6.27; and N, 9.68. Found: C, 53.13; H. 6.24; and N, 9.32.

When examined by HPLC (see description for FIG. 8 and Example 11, below), the product was found to be about 10% bis acid, 45% bis ester and 45% mono acid monoester. This is actually the contrast agent used for the FIG. 6 MRI image.

EXAMPLE 7

PREPARATION OF THE GADOLINIUM (III) CHELATES OF BIS(PHENYLALANINE) AND ITS ESTERS (a) A solution of 0.176 g (0.25 mmol) of DTPA-bis (phenylalanine) in 4 mL of water was treated with 0.093 g of GdCl$_3$ (Aldrich Chemical Co., Milwaukee, Wis.). The pH of the resulting solution adjusted to 7.0 with aqueous sodium hydroxide solution. The volume was adjusted to 5.0 mL with water, and this solution was filtered through a 0.22 micron sterile filter into a sterile serum vial. The resulting 0.05M solution is suitable for imaging in small animals.

The T1relaxation time at 0.25 Tesla magnetic field strength and 37° C. of a fivefold dilution of the above solution was 21 ms.

(b) The DTPA-bis(phenylalanine) mono and bis esters were prepared in a similar fashion.

EXAMPLE 8

MAGNETIC RESONANCE IMAGING OF A RAT USING Gd-DTPA-BIS(PHENYLALANINE)

A 300-g male Sprague-Dawley rat was anesthetized with an intraperitoneal injection of a mixture of ketamine and diazepam, and a catheter was inserted into a lateral tail vein. The rat was then placed in a 5-cm inside diameter (i.d.) imaging coil in the bore of a 2-Tesla imager-spectrometer system (GE CSI; General Electric Co., Fremont, Calif.). A T1-weighted spine-cho image of the animal's abdomen in the coronal plane was then obtained (TR 300 ms; Te 6 ms; 128–256 image matrix; NEX=4; 3 mm slice thickness). Next, 0.6 g of the Gd-DTPA-bis(phenylalanine) solution described in Example 7 was injected via the catheter. A series of post-injection images were obtained. The images displayed an initial enhancement in the liver and heart. As this enhancement decreased somewhat with time, increased intensity in the rat's small intestine then was observed, indicating hepatobiliary transport of the contrast agent. Intensity data are summarized below. The intensity values show some fluctuations due to breathing motion and other small artifacts. See also, FIGS. 5A and 5B.

TABLE 2

IMAGE REGION-OF-INTEREST % ENHANCEMENT

| Time | Liver | Heart | Muscle |
|---|---|---|---|
| (min post-injection) | | | |
| 0–3 | 51 | 42 | 14 |
| 5–8 | 60 | 27 | 3 |
| 15–18 | 47 | 25 | 12 |
| 25–38 | 50 | 22 | 12 |
| 45–48 | 34 | 9 | 10 |
| 60–63 | 33 | 12 | 2 |

EXAMPLE 9

MAGNETIC RESONANCE IMAGING OF A RAT USING Gd-DTPA-BIS(PHENYLALANINE ETHYL ESTER)

The imaging was carried out analogously to Example 8. Intensity data are summarized below. See also, FIGS. 6A and 6B.

TABLE 3

IMAGE REGION-OF-INTEREST % ENHANCEMENT

| Type | Liver | Heart | Skeletal Muscle |
|---|---|---|---|
| (min post-injection) | | | |
| 0-3 | 70 | 86 | 50 |
| 5-8 | 109 | 46 | 30 |
| 15-18 | 113 | 66 | 31 |
| 25-38 | 99 | 48 | 26 |
| 45-48 | 71 | 49 | 16 |
| 60-63 | 44 | 25 | 16 |

EXAMPLE 10

MAGNETIC RESONANCE IMAGING OF MICE USING Gd-DTPA-BIS(PHENYLALANINE) (BIS PHE ACID about 100%)

Figure 7:
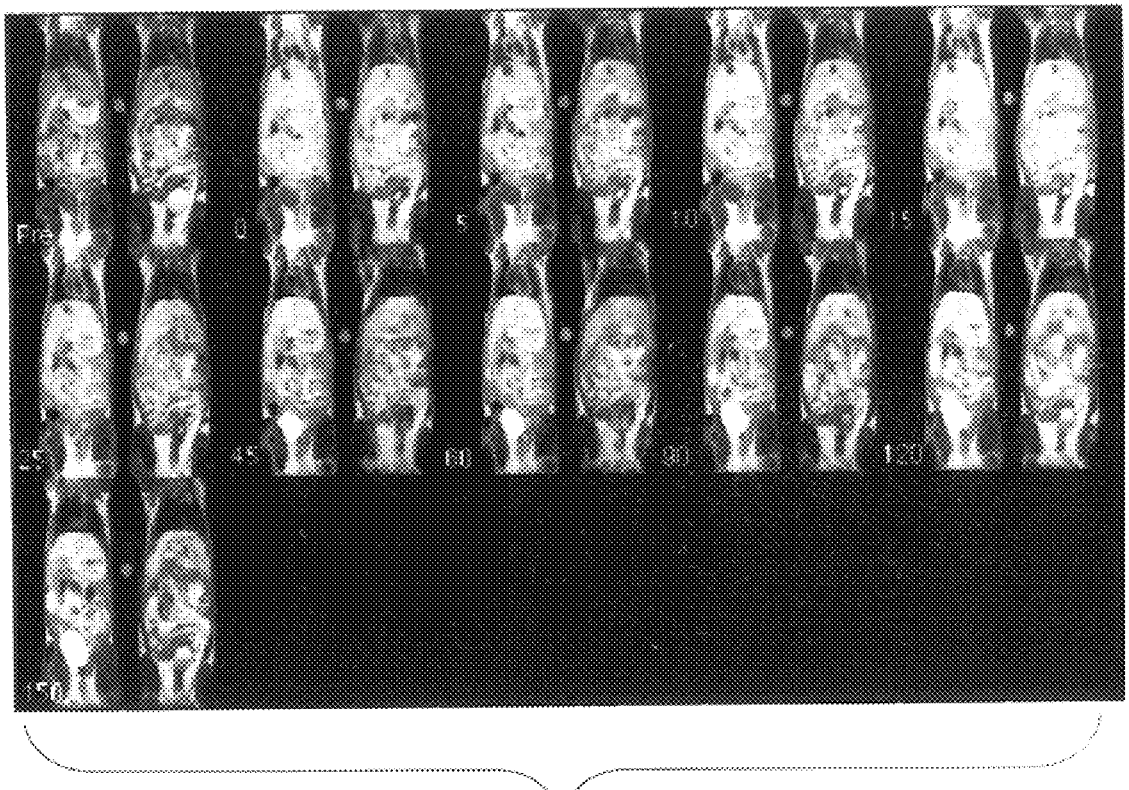
FIG. 7 is a photograph of the T1-weighted magnetic resonance images of two mice side-by-side at various times (indicated in min) after simultaneous injection of Gd-DTPA-bis(phenylalanine) (i.e. bis acid) described in Example 8 below, at approximately 0.1 mmol/kg dose. The images are 2 mm thick slices in a coronal plane at the level of the heart. The heart, liver and intestines are evident.

Two male BALB mice were imaged side by side in the same apparatus and using the same conditions as found in Example 8, except that the slice thickness was 2 mm. See FIG. 7 and accompanying description. Over the illustrated time course from 0 min to 2.5 hr, the contrast agent can be seen to localize first in the liver (e.g., at 2 min), then in the gall bladder (at 90 min, for example), and then in the intestinal lumen (2–2.5 hr). It can also be seen in the urinary bladder.

EXAMPLE 11

COMPARATIVE MRI DATA IN MICE

Figure 8:
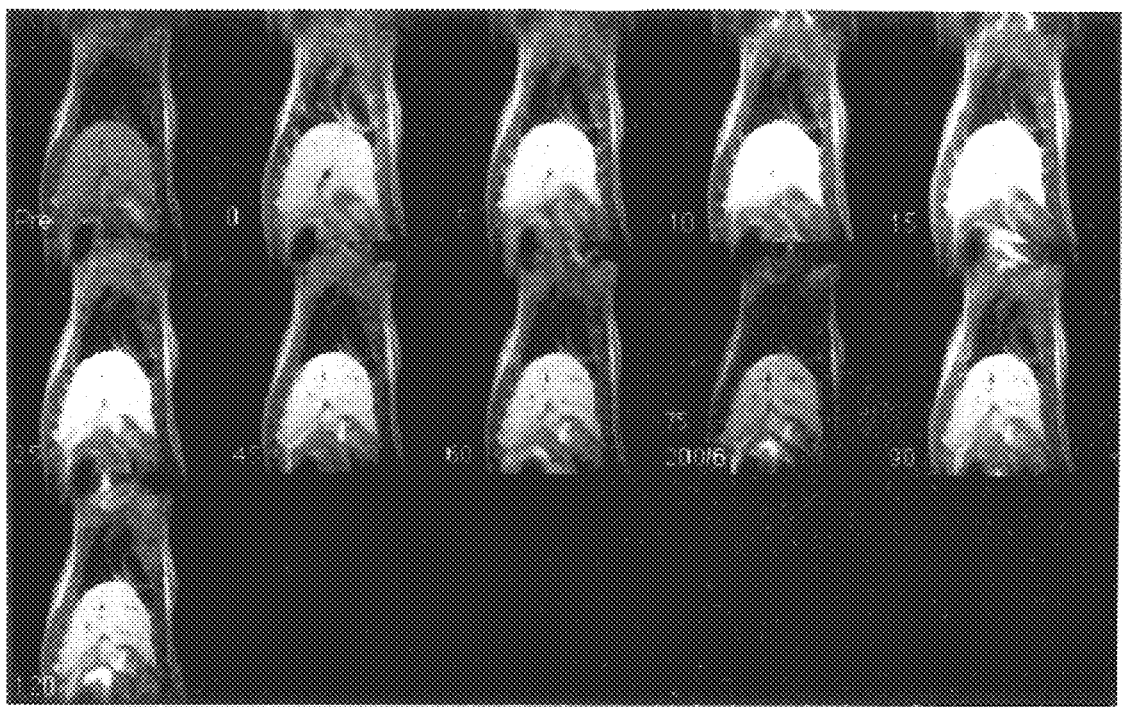
FIG. 8 is a photograph of T1-weighted magnetic resonance images as obtained for FIG. 6 except that a different preparation of Gd-DTPA-bis(phenylalanine ethyl ester) was employed.
Figure 9:
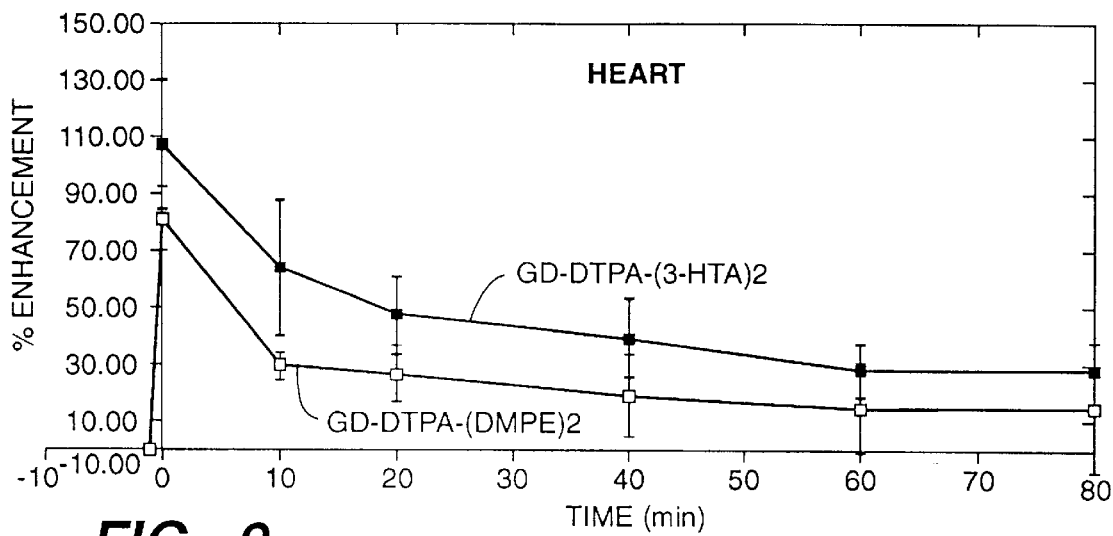
FIGS. 9–13 are each a graphic representation of MRI imaging in heart, lung, kidney, liver and skeletal muscle tissue, respectively, showing % enhancement versus time (min) for Gd(III)-DTPA-(3HTA)₂ and for Gd(III)-DTPA-(DMPE)₂.
Figure 10:
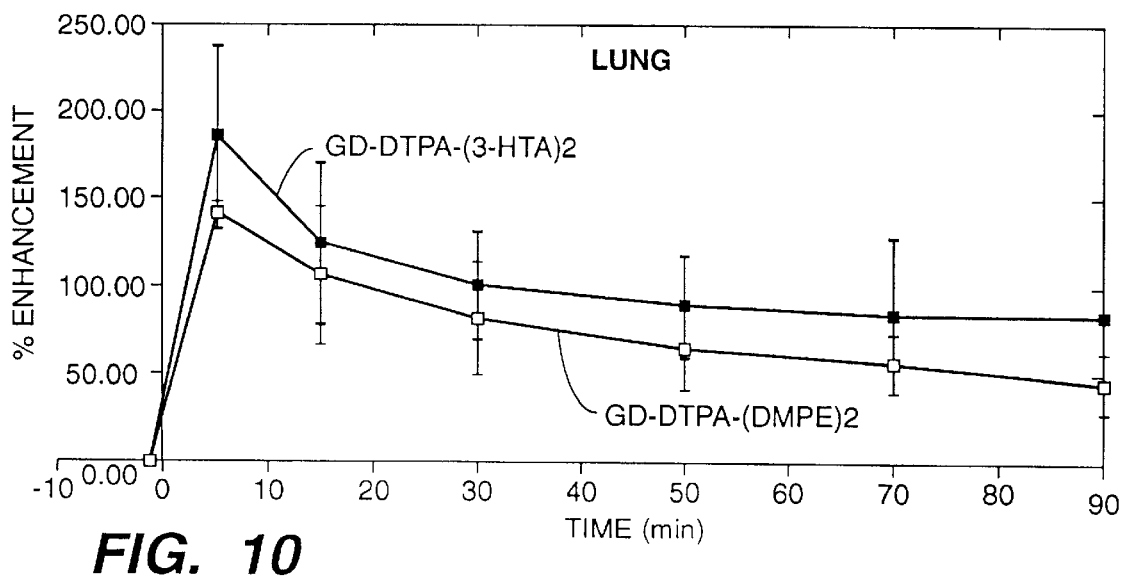

FIG. 8 is a photograph of T1-weighted magnetic resonance images obtained as in FIG. 6, except that a different preparation of Gd-DTPA-bis(phenylalanine ethyl ester) (sometimes abbreviated Gd-DTPA-(PheOEt)$_2$) was used.

When examined by HPLC [4.6×150 mm PRP-1 column; mobile phase 25 mM ammonium formate in water (Solvent A) and 50/50 (v/v) acetonitrile/water (Solvent B), programmed from 10% B to 95% B over 15 min, then holding at 95% B; flow rate 1 ml/min]; UV and/or radioisotope detector, the material used as a contrast agent in FIG. 6 was found to have partially hydrolyzed to a mixture of Gd-DTPA-(PheOEt)$_2$ (i.e. bis ester) (ca. 45%); Gd-DTPA-(PheOEt)(Phe) (i.e. mono ester, mono acid) (ca. 45%); and Gd-DTPA-(Phe)$_2$ (i.e. bis acid) (ca. 10%).

Freshly prepared material, whose pH was carefully adjusted to neutrality, and which was stored in the cold, was determined to be about 90% Gd-DTPA-(PheOEt)$_2$, the remainder being mostly Gd-DTPA(PheOEt) (Phe).

The more pure preparation gave heart and liver enhancement (74% and 163%, respectively) as shown in FIG. 6 (84% and 53%, respectively). Thus, the degree of liver enhancement was greater by a factor of about three.

These results suggest that esterified DTPA-amino acid chelates may be particularly advantageous for higher contrast enhancement.

EXAMPLE 12

PREPARATION OF DTPA-BIS(D-PHENYLALANINE ETHYL ESTER)

DTPA-bis(D-phenylalanine ethyl ester) was prepared analogously to the corresponding L-isomer from D-phenylalanine ethyl ester and DTPA-bis(anhydride) (Example 4). The yield was 65%.

Anal. Calcd for C$_{36}$H$_{49}$N$_5$O$_{12}$: C, 58.13; H, 6.64; and N, 9.42. Found: C, 57.87; H, 6.55; N, 9.48.

EXAMPLE 13

PREPARATION OF DTPA-BIS (PHENYLALANINE METHYLAMIDE)

A suspension of 2.07 g (10.43 mmol) of L-phenylalanine methyl amide hydrochloride in ethyl acetate (75 mL) was treated with a saturated aqueous solution of sodium carbonate (20 mL). The resulting solution was extracted with ethyl acetate (2×75 mL), and the combined organic extracts were dried over anhydrous sodium sulfate. The drying agent was removed by filtration, and the filtrate was concentrated to an oil using a rotary evaporator. This residue was further dried over P$_2$O$_5$ under high vacuum overnight to yield 1.72 g of the amine as a white solid.

A solution of the dried amine in anhydrous pyridine (15 mL) was combined with DTPA-bis(anhydride) (1.80 g, 5.04 mmol) under argon. The reaction mixture was heated at reflux in an oil bath (95° C.) for 60 min. The mixture was allowed to cool to room temperature (0.5 hr) and was concentrated in vacuo to yield a viscous residue. This material was dissolved in 100 mL of water, and the water then was evaporated in vacuo to yield a yellow oil. The oil was dissolved in a minimum amount of a solution of water in methanol (20% v/v) and treated with acetonitrile until a small amount of precipitate was observed. The precipitate was removed by filtration (0.45 μm membrane filter), and the filtrate was concentrated under reduced pressure. This procedure was repeated twice more, discarding the precipitate each time. Finally, the residue obtained by evaporation of the solvent was dissolved in a solution of water in methanol (10 mL, 20% v/v), and the desired product was precipitated by addition of a minimum amount of acetonitrile. The resulting white suspension was cooled in a freezer (−20° C.) overnight, and the solvent then was removed by decantation. The product was dried under high vacuum (0.05 torr, 48 hr) over P$_2$O$_5$ and NaOH to afford 1.38 g (39%) of an analytically pure white solid.

Anal. Calcd. for C$_{34}$H$_{47}$N$_7$O$_{10}$.0.5 H$_2$: C, 56.50; H, 6.69; N, 13.57. Found: C, 56.34; H, 6.61; N, 13.66.

EXAMPLE 14

PREPARATION OF DTPA-BIS (PHENYLALANINE AMIDE) AND DTPA-BIS (PHENYLALANINE DIMETHYLAMIDE)

The title compounds (i.e. DTPA-bis(phenylalanine amide) and DTPA-bis(phenylalanine dimethylamide) were prepared analogously to the dimethylamide compound of Example 13 from DTPA-bis(anhydride) and L-phenylalanine amide hydrochloride and L-phenylalanine dimethylamide; in 20% and 59% yields, respectively.

Calcd. for the amide $C_{32}H_{43}N_7O_{10} \cdot 2H_2O$: C,53.25; H,6.57; N,13.58. Found: C,53.43; H,6.30; N,13.59.

Calcd for the dimethylamide $C_{36}H_{51}N_7O_{10}$: C,56.90; H,7.03; and N,12.90. Found: C,56.82; H,6.74; N,12.76.

EXAMPLE 15

PREPARATION OF DTPA-BIS(3-HYDROXYTYRAMIDE) ("DTPA-(3-HTA)$_2$")

DTPA-bis(anhydride) (3.57 g; 1.00 mmol; Aldrich Chemical Co., Milwaukee, Wis.) was suspended in 25 mL of anhydrous dimethylformamide (DMF; Aldrich) and treated with dopamine (3.78 g; 2.00 mmol; Fluka-USA, Ronkonkoma, N.Y.) and di-isopropylethylamine (5.2 g; 4.0 mmol; Aldrich Chemical Co.) This mixture then was heated briefly to 100° C. and sonicated for several minutes to dissolve the bulk of the solid. After stirring for 4–6 hr at 50–60° /cm, a deep yellow solution was produced. The reaction mixture then was allowed to cool to room temperature.

After stirring at ambient temperature overnight, the reaction mixture was concentrated on a rotary evaporator at 50° C. to a volume of about 10 mL. The odor of di-isopropylethylamine was absent at this point. Water (25 mL) was added, and the resulting solution was washed twice with 20 mL portions of ethyl ether to remove the remaining DMF. The water then was removed in vacuo to yield a beige paste. This material was suspended in 10–20 mL of absolute ethanol and dried by azeotropic distillation of aqueous ethanol in vacuo. The crude product (7 g; 97% of theory) was a gritty, off-white, hygroscopic solid.

An analytical pure sample (1.76 g; 26% of theory) was isolated by preparative high-pressure liquid chromatography (HPLC) using a 4.6×150 mm Microsorb C-18 reversed phase column (Rainin Instrument Co., Emeryville Calif.). The mobile phase (1 mL/min flow rate) was a linear gradient from 5 to 50% acetonitrile in water over 12 min An acidic pH was maintained by the presence of 0.1% v/v trifluoroacetic acid in both components of the mobile phase. A UV detector measuring absorbance at 276 nm was used. The retention time of the product was 13.5 min under these conditions. $^1$H NMR spectrum: δ6.75, m, 6H; δ3.81–2.62, 26H, aliphatic H, not further assigned.

Liquid secondary ion mass spectrum (LSIMS) [M—H]= 662 (theory 662).

EXAMPLE 16

PREPARATION OF DTPA-BIS(3,4-DIMETHOXYPHENETHYLAMIDE) ("DTPA-(3,4-DMPE)$_2$")

Equimolar amounts of DTPA-bis(anhydride) and 3,4-dimethoxyphenethylamine (Aldrich Chemical Co.) were contacted as above in Example 15 to give crude product in ca. 100% yield. This material was purified by preparative HPLC to produce 1.23 g (17%) of the title compound.

$^1$H NMR spectrum: δ6.80, m, 6H; δ3.82, s, 6H, CH$_3$O—; δ3.80, s, 6H; CH$_3$O—; δ3.45–2.76, 26H, aliphatic H not further assigned.

LSIMS mass spectrum: [M—H]-=718 (theory 718).

EXAMPLE 17

PREPARATION OF GD-DTPA-(3-HTA)$_2$

Solutions of Gd-DTPA-(3-HTA)$_2$ for imaging experiments were prepared by reacting DTPA-(3-HTA)$_2$ in aqueous solution with a stoichiometric amount of GdCl$_3$ dissolved in water. After about 90% of the GdCl$_3$ had been added, the pH of the reaction mixture was adjusted to between 5 and 6 with aqueous NaOH solution. Xylenol orange indicator (1 drop of a 1 mg/mL aqueous solution) then was added, and GdCl$_3$ solution was added dropwise until the indicator changed from yellow to violet (at pH <6). The pH then was adjusted to between 7 and 8 with aqueous NaOH and, if. necessary, aqueous HCl solution. The reaction mixture was passed through a 0.22 μm sterile filter into a sterile serum vial. The final concentration ranged from 0.02 to 0.5M, depending upon the initial concentrations of the reactants and the volumes of base and acid added for pH adjustment.

A sample of product for mass spectral analysis was obtained by HPLC (4.6×150 PRP-1 column; 1 mL/min flow rate; 5–45% over 15 min acetonitrile-in-water gradient). The LSIMS [M+H]$^+$ parent ion peaks were observed from 815–824, with the maximum intensity at 819. The ratios of peak intensities were those predicted by theory $C_{30}H_{38}GdN_5O_{12}$.

EXAMPLE 18

PREPARATION OF GD-DTPA-(3,4-DMPE)$_2$

This chelate was prepared analogously to Gd-DTPA-(3-HTA)$_2$, as in Example 17 above, from DTPA-(3,4-DMPE)$_2$ and GdCl$_3$.

EXAMPLE 19

IN VIVO MAGNETIC RESONANCE IMAGING USING GD-DTPA-(3-HTA)$_2$ and GD-DTPA-(3,4-DMPE)$_2$ Magnetic resonance imaging was carried out using a CSI 2-Tesla imager (GE, Inc., Fremont, Calif.) equipped with a 5-cm diameter distributed-capacitance imaging coil. A T1-weighted (TR 300/TE 6; NEX 4) spin-echo sequence was used. The image matrix was 128×256, the slice thickness was 3 mm, and the field of view was 90 mm. anterior (heart level) and posterior (kidney level) coronal image planes were used.

Sprague-Dawley rats (250–350 g; n=4 for each contrast agent) were anesthetized with ketamine (90 mg/kg) and diazepam (10 mg/kg) and fitted with an intravenous catheter in a lateral tail vein. Anesthesia was maintained during imaging using pentobarbital delivered via an intraperitoneal catheter.

The anesthetized animal was placed in the imaging coil and secured with tape. The coil containing the animal then was placed in the magnet bore, and the magnetic field was shimmed. Pre-contrast images were obtained. The contrast agent (100 μmol/kg) then was injected via the tail-vein catheter, and additional images were obtained at various intervals for up to 90 min post injection.

Contrast agent enhancement was determined by measuring the mean signal intensity (SI) in operator-designated regions of interest (ROI). These were normalized to the pre-injection value for each ROI according to the following formula:

% Enhancement=$100\times(SI_{post}-SI_{prc})/SI_{prc}$ function of time in heart, lung, kidney, liver, and skeletal muscle, FIGS. 9–13 respectively, for each of the contrast agents are illustrated, Gd-DTPA-(3-HTA)$_2$ also tended to produce higher lung enhancement (186%±51% vs. 141%±4%). However, the differences between the effects produced by the two agents was smaller than in heart (cf. FIGS. 9 and 10).

Figure 11:
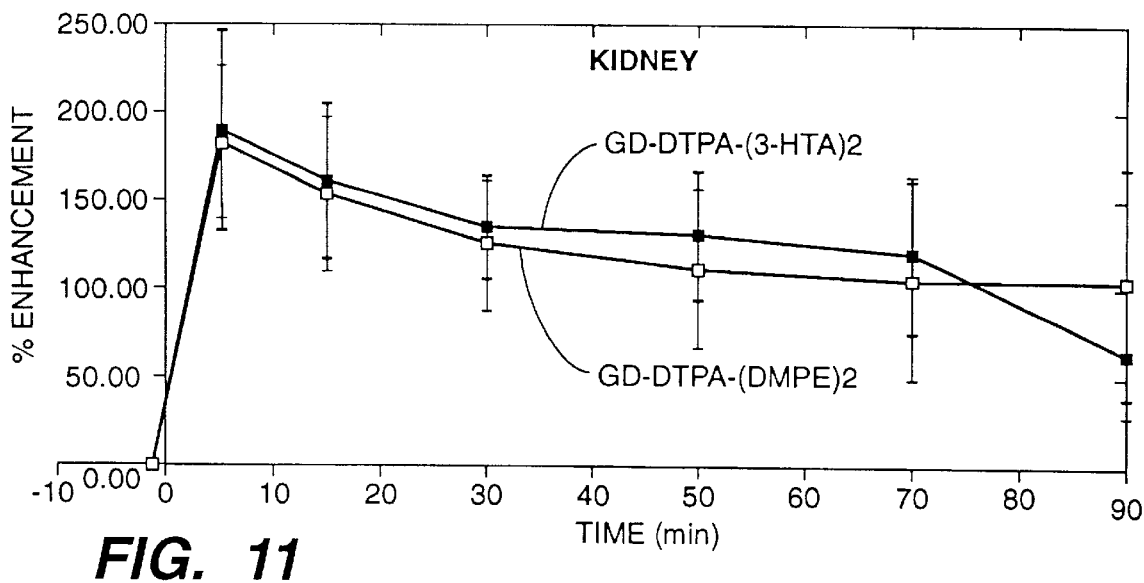

There was no significant difference in kidney enhancement (FIG. 11). Both agents produced ca. 175% enhancement 5 min after injection. The level of enhancement fell slowly over 70 min to about 100%.

Figure 12:
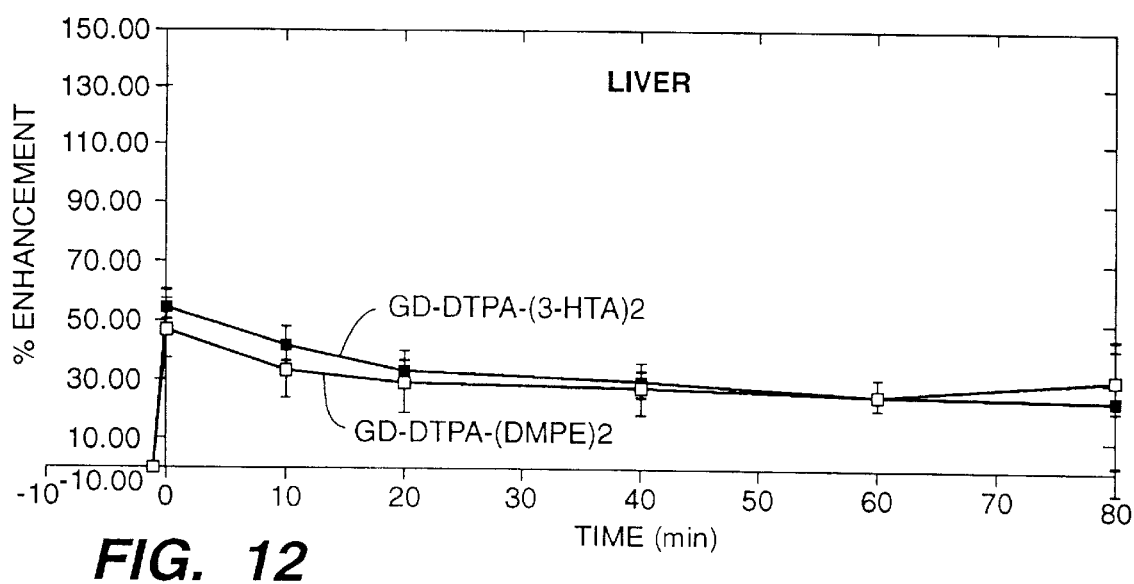

About 50% enhancement was produced in the liver by both agents immediately post-injection (FIG. 12). Additionally, the time course of enhancement was very similar for both agents, with the enhancement level falling to about 30% during the first 20 min post injection.

Figure 13:
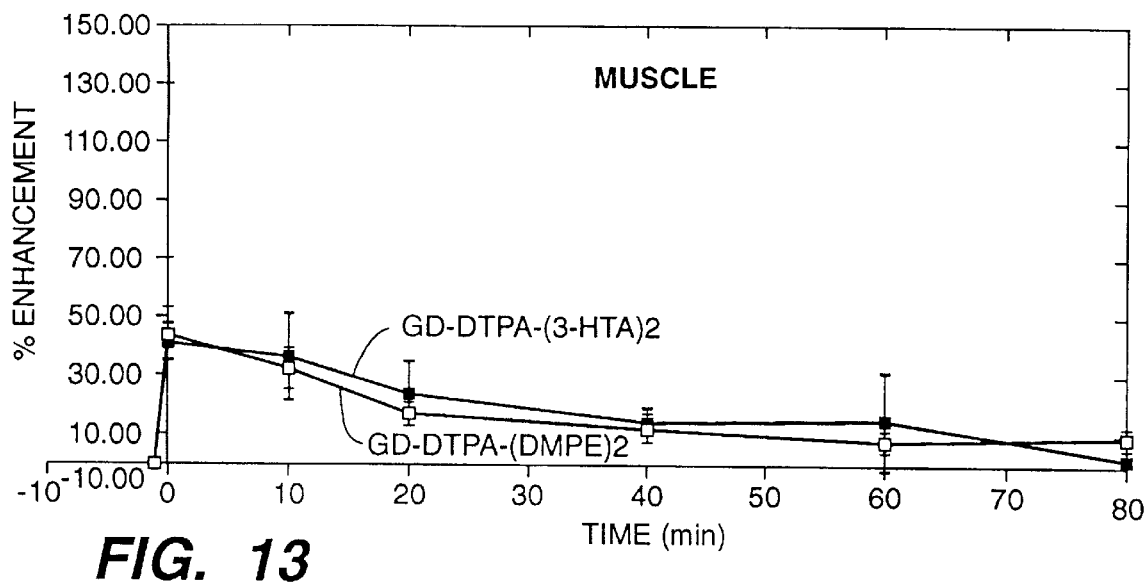
Figure 16:
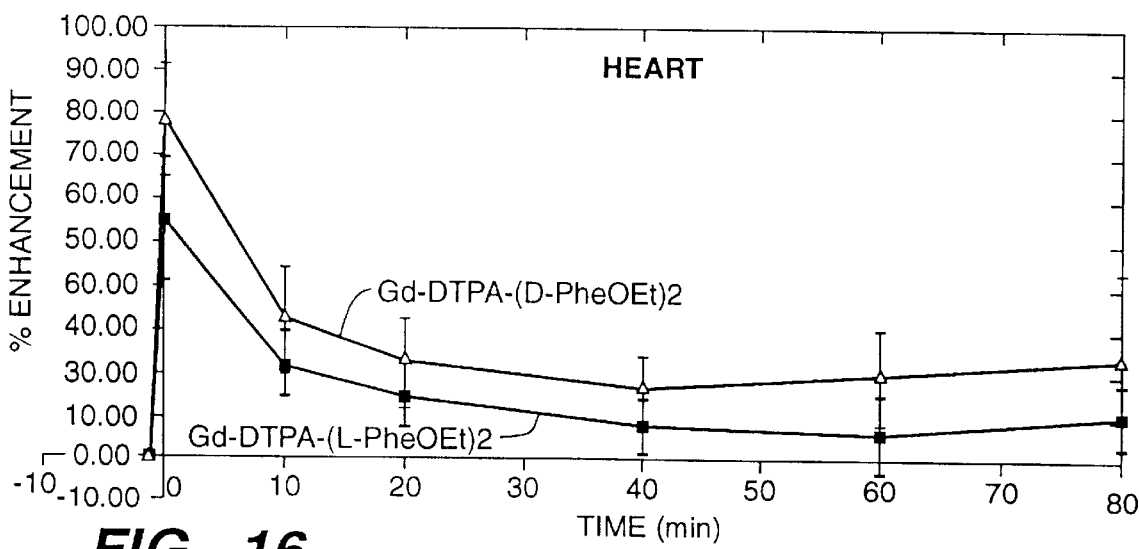
FIGS. 16–20 are each a graphic representation of MRI imaging in heart, lung, kidney, liver and skeletal muscle tissue, respectively, showing % enhancement versus time (min) for Gd(III)-DTPA-(L-PheOEt)₂ (i.e. Gd(III)-DTPA-bis(L-phenylalanine ethyl ester)) and for Gd(III)DTPA-(D-PheOEt)₂ (i.e. Gd(III)-DTPA-bis(D-phenylalanine ethyl ester)).
Figure 14A:
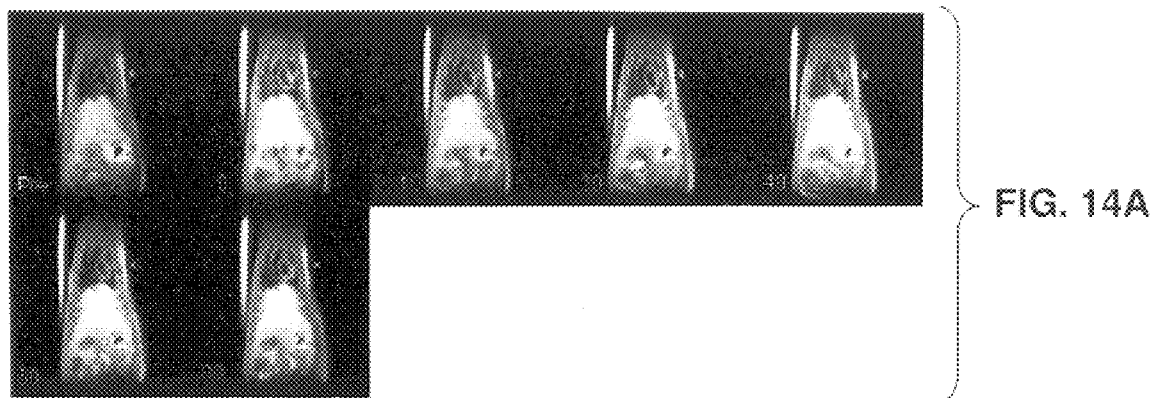
FIG. 14A is a photograph of T1-weighted MRI images of a rat as obtained (as indicated in min) for FIG. 5 using Gd(III)-DTPA-(3HTA)₂.
Figure 14B:
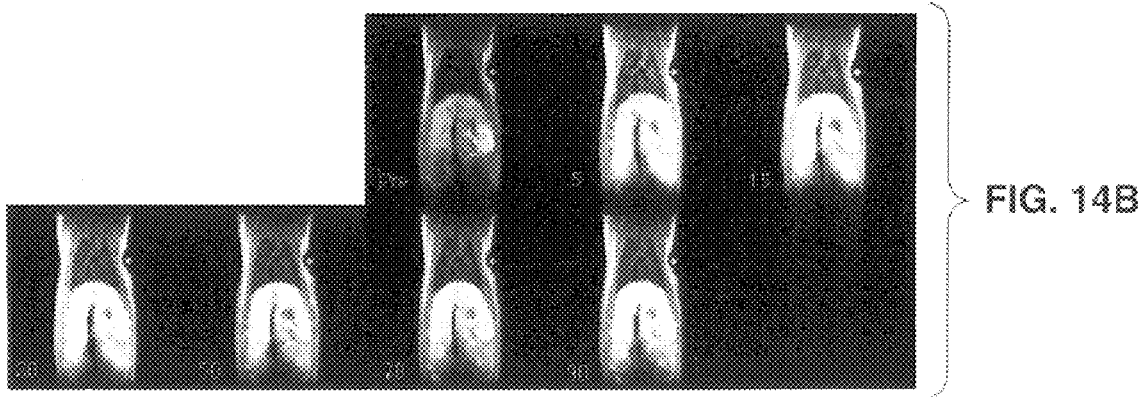
FIG. 14B is a photograph of a second coronal plane at the level of the kidneys, as shown in FIG. 14A.
Figure 15A:
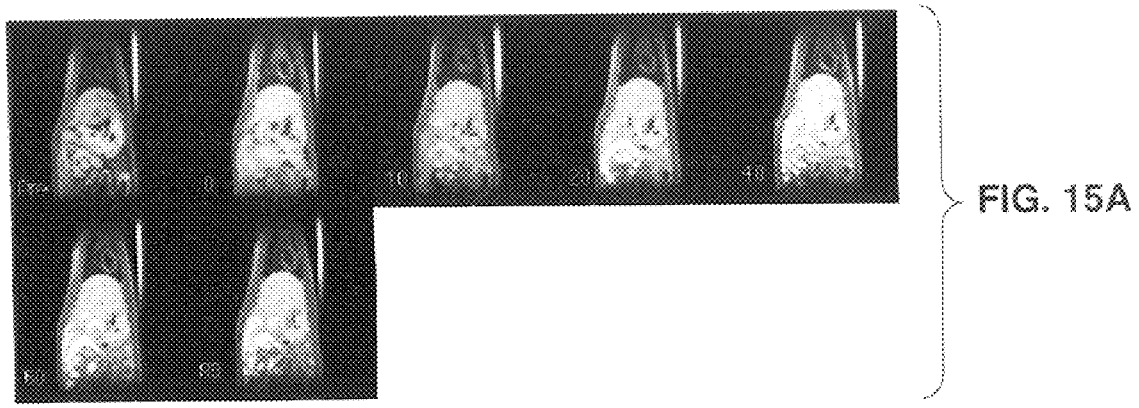
FIG. 15A is a photograph of T1-weighted MRI images of a rat as obtained (as indicated in min) for FIG. 5 using Gd(III)-DTPA-(DMPE)₂.
Figure 15B:
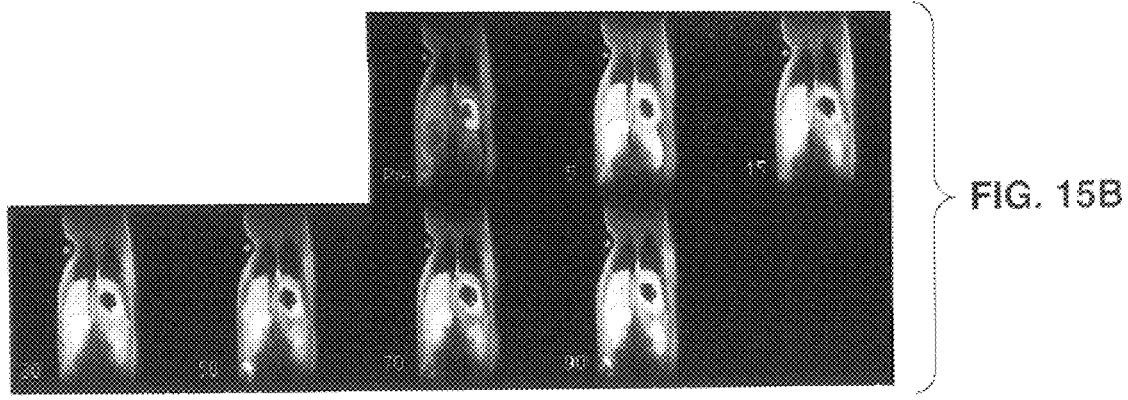
FIG. 15B is a photograph of a second coronal plane at the level of the kidneys, as shown in FIG. 15A.
Figure 17:
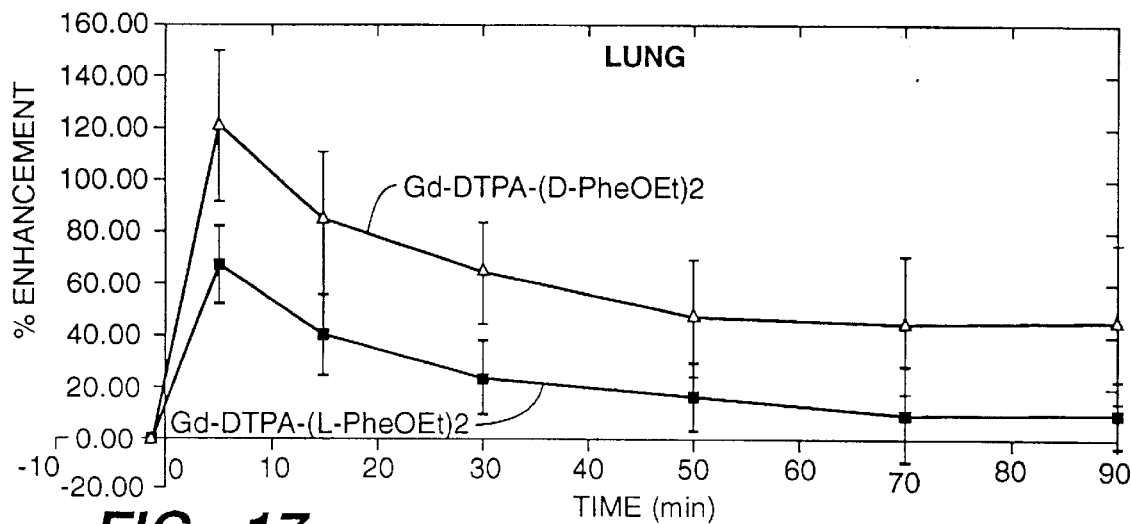
Figure 18:
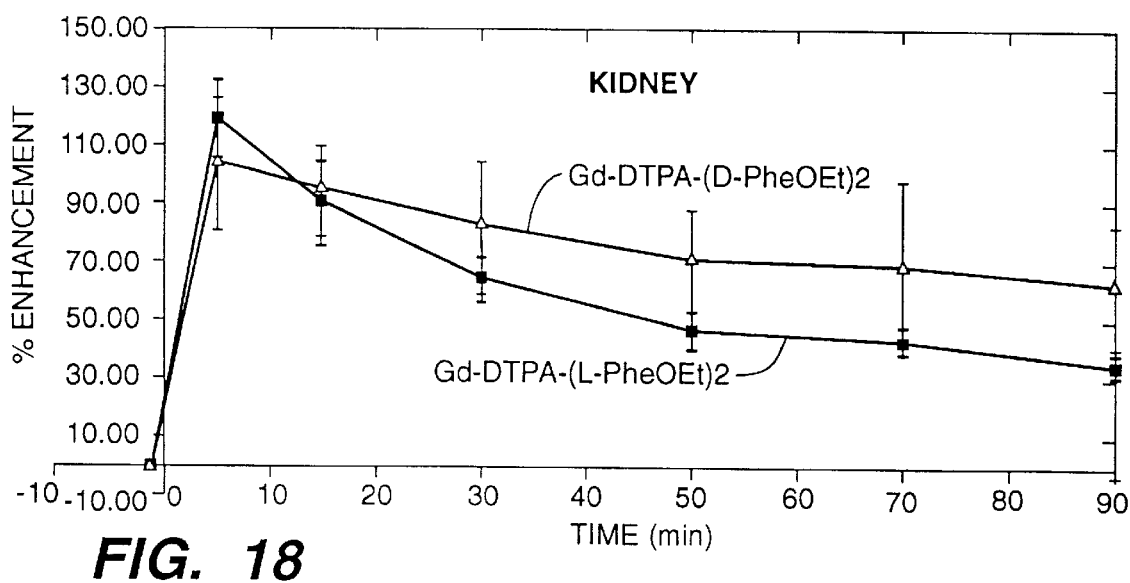
Figure 19:
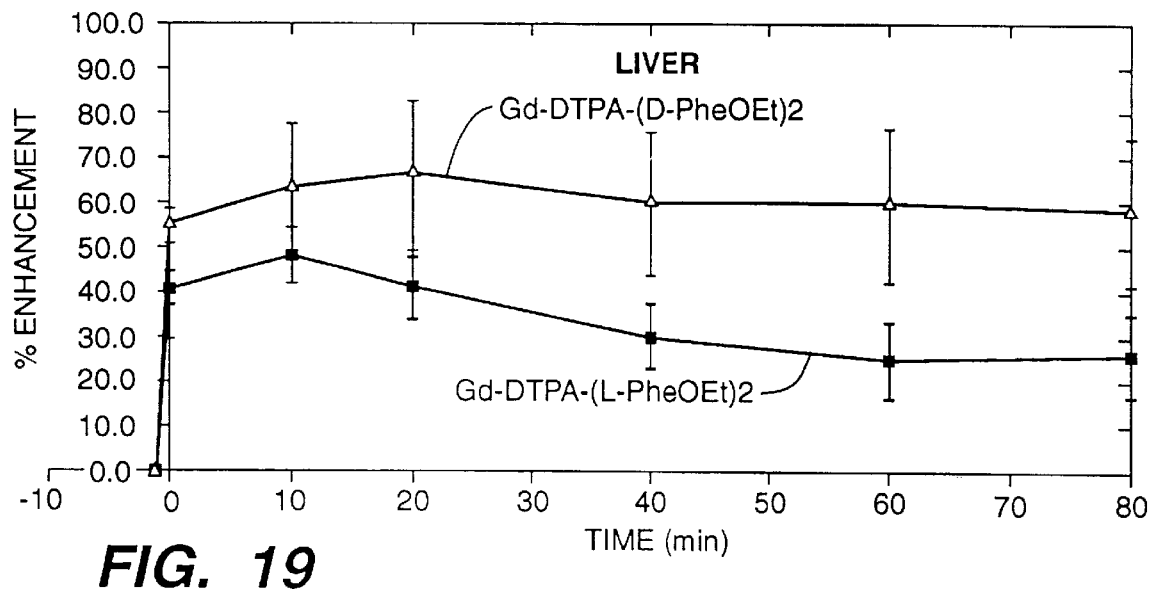
Figure 20:
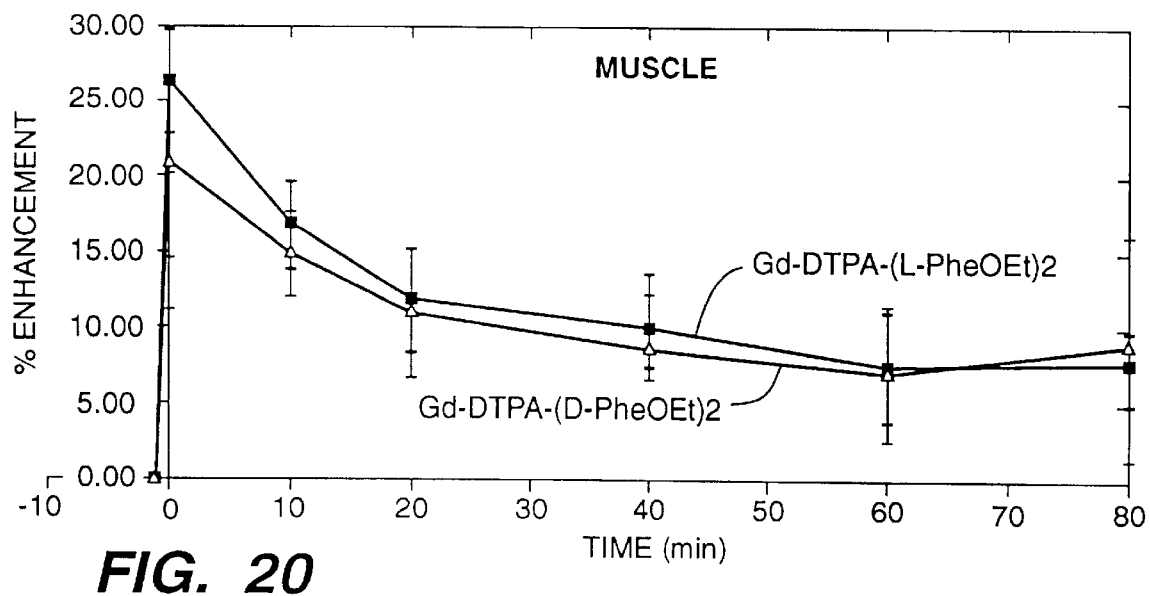

Skeletal muscle displayed peak enhancement of about 40% immediately post-injection. The enhancement-time curves for both agents were almost identical; each fell almost to pre-injection levels over 80 min (FIG. 13).

Representative images using each agent are shown in FIGS. 14A and 14B and 15A and 15B as MRI photographic images.

EXAMPLE 20

IN VIVO MAGNETIC RESONANCE IMAGING USING

GD-DTPA-(L-PheOEt)$_2$ and GD-DTPA-(D-PheOEt)$_2$

The magnetic resonance imaging characteristics of the two contrast agents Gd-DTPA-(L-PheOEt)$_2$ and Gd-DTPA-(D-PheOEt)$_2$ were compared as in the previous Example using groups of 4 and 5 animals, respectively. FIGS. 16 to 20 illustrate the contrast enhancement versus time behavior for each agent in heart, lung, kidney, liver and skeletal muscle, respectively.

Figure 21A:
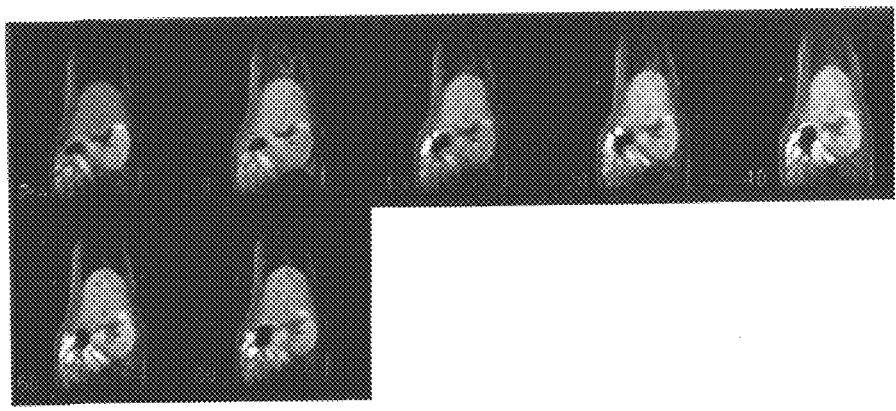
FIGS. 21 (A and B) and 22 (A and B) are each T1-weighted MRI photographic images of a rat as obtained for FIGS. 14 and 15 using Gd(III)-DTPA-(L-PheOEt)₂ (FIG. 21) or Gd(III)-DTPA-(D-PheOEt)₂ (FIG. 22); except that the dose level was 0.05 mmol/kg.
Figure 21B:
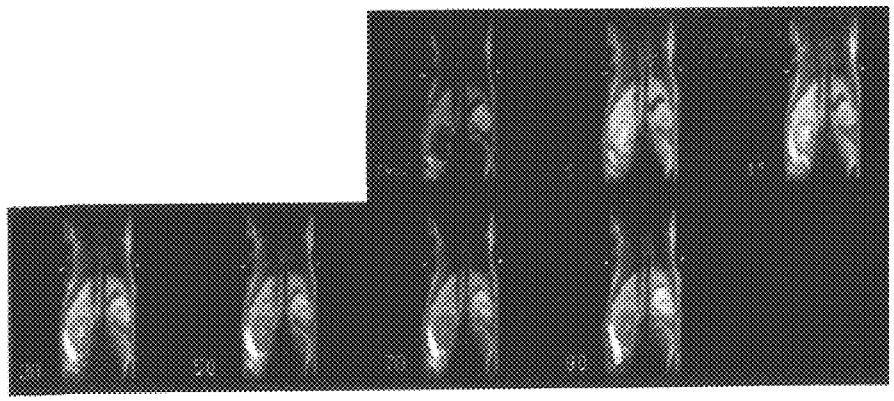
Figure 22A:
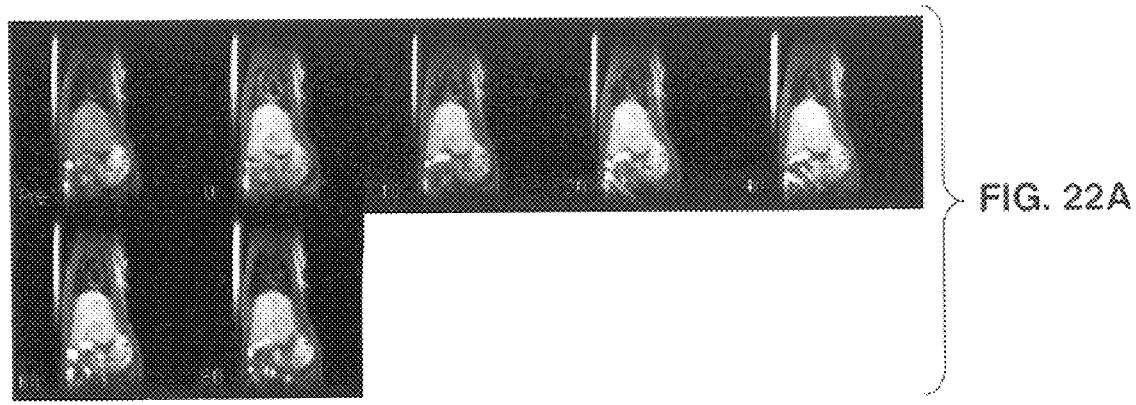
Figure 22B:
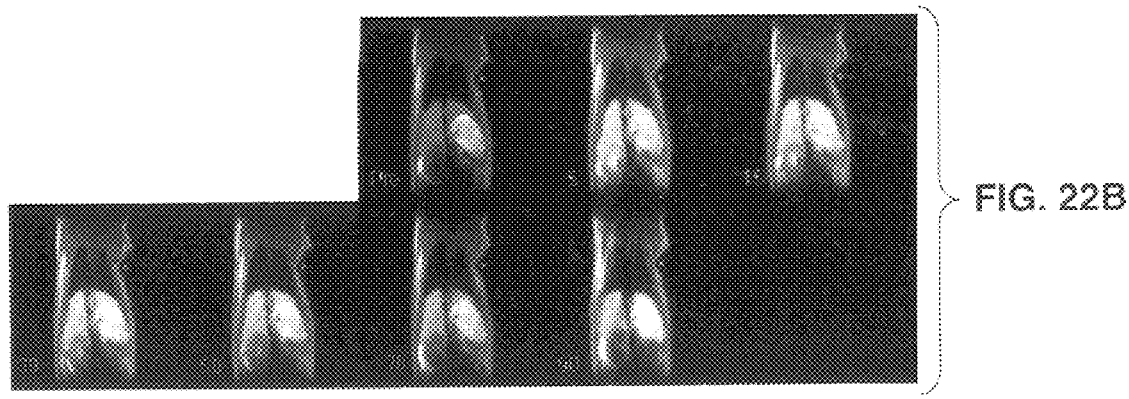

Representative images using each agent are shown in FIGS. 21A and 21B and 22AA and 22B as MRI photographic images.

EXAMPLE 21

HYDROLYSIS OF GD-DTPA-(L-PheOEt)$_2$ AND Gd-DTPA-(D-PheOEt)$_2$ IN pH 7.4 BUFFER AND RAT PLASMA

The rates of hydrolysis of the esters in rat plasma or pH 7.4 HEPES buffer were determined by addition of 10% by volume of Gd-153 radiolabeled 0.025M chelate solution and incubation at 0 or 25° C. Aliquots were withdrawn at various time intervals and examined by HPLC [PRP-1 column; water-acetonitrile gradient; 25 mM ammonium formate, pH 7 mobile phase].

The hydrolysis of either the LL- or DD-bis(ester) enantiomers to the corresponding mono(ester)—mono(acid) and thence to the bis(acid) in aqueous HEPES buffer at pH 7.4 and 25° C. is very slow, with half-times for each step of the order of days.

However, the LL-bis(ester) is very rapidly hydrolyzed in rat plasma to the mono(acid)-mono(ester) (see below). The latter compound is much more resistant to hydrolysis of the remaining ester, with essentially no reaction being observed within 2 hr at 25° C.

In contrast, the DD-bis(ester) is resistant to even the first step of ester hydrolysis under these conditions (see below).

| $t_{1/2}$ of Ester Hydrolysis in Rat Plasma | | |
|---|---|---|
| | @ 0° C. | @ 25° C. |
| Gd-DTPA-(L-PheOEt)$_2$ | 33 min | 0.3 min |
| Gd-DTPA-(D-PheOEt)$_2$ | None Detected | None Detected |

The relative stability of the bis(esters) toward hydrolysis in aqueous solution versus plasma suggest that the plasma reaction is enzyme-catalyzed. Furthermore, mono(acid)-mono(ester) is evidently a much poorer substrate, as its rate of hydrolysis is much slower. This may be due to the change in net charge (from 0 to 1) of the chelate and/or to a change in conformation of the molecule due to coordination of the Gd by the free phenylalanine carboxylate group.

Changing the stereochemistry of the amino acid portion of the chelate to the unnatural D-enantiomer caused the rate of ester hydrolysis in plasma to greatly decrease.

EXAMPLE 22

DETERMINATION OF RELATIVE AMOUNTS OF URINARY AND BILIARY EXCRETION

Male Sprague-Dawley rats were anesthetized with an intraperitoneal injection of mixture of ketamine (90 mg/kg) and diazepam (2 mg/kg), and fitted with a 23-gauge cannula placed in a lateral tail vein. Next, a midline incision and small lateral cut over the bile duct were made, and the bile duct was exposed. Two loose ties were placed proximally on the bile duct. A small nick was made distally, and the bile duct was cannulated with a 15-cm length of PE-10 polyethylene tubing, which was secured with the two ties.

A second piece of tubing was placed in the urinary bladder and secured with a purse-string suture. The flap of the abdominal wall was closed, and the incision was covered with gauze.

Heparinized (1 unit/mL) saline was infused at a rate of 0.075 mL/min via the iv catheter. After a 15 min stabilization period, the infusion was interrupted long enough to deliver a bolus dose (0.1 mmol/kg) of Gd-153 labeled contrast agent, and then resumed. Samples of bile and urine were collected in tared tubes at regular intervals before and after injection of radiolabeled agent. The net weights of these samples were determined. The amount of Gd-153 present in each sample was determined by counting in a chamber gamma counter. The raw counts were corrected for background and normalized to the total amount of Gd-153 injected.

The Table below summarizes the results (cumulative 1 hr excretion; average of 3 animals) obtained for some of the agents described in the prior Examples:

| One-Hour Cumulative Excretion | | |
|---|---|---|
| | Biliary | Urinary |
| Gd-DTPA-(L-Phe)$_2$ | 9.3 ± 1.3 | 66.5 ± 8.7 |
| Gd-DTPA-(L-PheOEt)$_2$ | 30.5 ± 7.4 | 46.9 ± 8.0 |

-continued

One-Hour Cumulative Excretion

|  | Biliary | Urinary |
|---|---|---|
| Gd-DTPA-(D-PheOEt)$_2$ | 51.3 ± 5.1 | 39.2 ± 5.5 |
| Gd-DTPA-(L-PheNHCH$_3$)$_2$ | 3.5 ± 0.4 | 70.9 ± 6.5 |

Alternatively, the radio-labeled contrast agent can be delivered without any unlabeled carrier. In this case, essentially all of the paramagnetic metal ion is present as the gamma-emitting isotope, and the absolute dose of chelate is approximately $1 \times 10^{-5}$ mmol/kg. A significantly higher biliary excretion level at a tracer dose, compared to that of a carrier-added dose, suggests that the latter may have exceeded the capacity of the hepatobiliary transport system.

EXAMPLE 23

DETERMINATION OF RELATIVE AMOUNTS OF URINARY AND FECAL ELIMINATION

A Sprague-Dawley rat was anesthetized with an intraperitoneal injection of a mixture of ketamine (90 mg/kg) and diazepam (2 mg/kg). A 23-gauge cannula placed in a lateral tail vein was used to deliver a bolus intravenous dose (0.1 mmol/kg) of chelate labeled with Gd-153 (ca. 0.03 mCi/mmol). After injection, the rat was placed in a chamber gamma counter to determine the count rate of the injected dose. The animal then was housed in a metabolic cage where urine and feces could be separately collected. The animal itself, its urine, and its feces were counted at various time points up to five days post injection. Typically, a group of four animals was used for each compound tested. The mean values for residual activity in the body, and cumulative fecal and urinary activities, expressed as a per cent of the injected dose, were determined.

As in Example 22, tracer versus carrier-added doses were sometimes compared to check for possible saturation of biliary transport at the higher dose.

Gd-DTPA-(L-PheOH)$_2$ at tracer dose gave values at 2.1%±0.2%, 80.7%±8.4%, and 14.1%±1.7% for residual, urinary, and fecal activity, respectively. The corresponding values for a 0.1 mmol/kg dose were 1.8%±0.1%, 81.1%±9.0%, and 12.0%±3.8%.

EXAMPLE 24

PREPARATION OF VARIOUS SUBSTITUTED PHENYLALANINE AND SUBSTITUTED TYROSINE DERIVATIVES (a) (L)-p-t-butylphenylalanine ((L)-p-t-butyl-PHE) was prepared via a Friedel-Crafts reaction employing (L)-phenylalanine and t-butyl alcohol. To a homogeneous solution of (L)-phenylalanine (33 g, 0.2 mol, dissolved in 55 mL of concentrated sulfuric acid) was added t-butyl alcohol (50 mL, 0.53 mol) at ambient temperature. The reaction temperature was kept at 30° C. or below during the addition of the alcohol. After stirring overnight, the reaction mixture was treated with water (100 mL) and extracted with ethyl acetate (100 mL) twice. The aqueous layer was cooled in an ice-water bath and the pH of the solution adjusted to 5.5 by the addition of 6.6M NaOH, causing precipitation of the amino acid. The solid, obtained after removal of the solvent from the filtrate, was dried in vacuo to obtain the expected product (13.9 g), (L)-p-t-butylphenylalanine, in 31% yield. Anal. Calcd. $C_{13}H_{19}NO_2.0.75 H_2O$: C, 66.50; H, 8.80; N, 5.97. Found: C, 66.46; H, 8.64; N, 5.81.

Methods for the preparation of (L)-p-t-butylphenylalanine have also been reported in the literature (see, e.g., Miyaka, A., et al., J. Takeda Res. Lab., 43:53–76, 1984).

(b) (L)-p-ethoxyphenylalanine ((L)-p-EtO-PHE) was prepared from N-t-boc-protected tyrosine essentially following a reported procedure (Mndzhoyan, O. L., et al., Khim. Farm. Zh., 5:4–7,1971). To N-t-boc-tyrosine (56.3 g, 0.2 mol) dissolved in DMSO (400 mL) and 20% aqueous sodium hydroxide (80 mL) was added diethyl sulfate (33.9 g, 0.22 mol) dropwise. The reaction temperature was maintained at 40–500° C. for about 3 hours. To the reaction mixture was added 6.0M hydrochloric acid (200 mL), and the mixture was kept at 50°–60° C. for about 3 hours. The mixture was then cooled down to ambient temperature, and treated with concentrated ammonium hydroxide until the pH of the resulting solution was adjusted to about pH 7. The precipitate was collected and dried in vacuo. The expected product, (L)-p-ethoxyphenylalanine, was obtained in 90% yield. The physicochemical properties of the (L)-amino acid were in agreement with reported literature values.

EXAMPLE 25

PREPARATION OF VARIOUS DTPA-BIS (AMINO ACID DERIVATIVES) FROM SYBSTITUTED PHENYLALANINE AND SUBSTITUTED TYROSINE

The amino acid derivatives of Example 24 were used to prepare a variety of corresponding DTPA-bis(amino acid derivatives). In particular, the various DTPA-bis(amino acid) derivatives were prepared from the reactions of DTPA-bis-anhydride (1 equivalent) with the various p-substituted amino acids (2.1 equivalents) in pyridine at 40–60 degrees Celsius for 4–6 hours under a nitrogen atmosphere. The brown residue, after removal of the pyridine, was purified by anion exchange column chromatography using an AG1x2 (formate) column (Bio-Rad, Richmond, Calif.). The p-substituted ligands were eluted out with 2.0M aqueous formic acid.

EXAMPLE 26

PREPARATION OF GD(III) COMPLEXES OF VARIOUS DTPA-BIS(AMINO ACID DERIVATIVES)

The DTPA-bis(amino acid derivatives) of Example 25 were used to prepare a variety of corresponding Gd(III) complexes substantially as described in Example 2. The gadolinium chelates were purified by reverse phase column chromatography using a CHP20P column (YMC, Wilmington, N.C.).

EXAMPLE 27

DETERMINATION OF BILIARY AND/OR FECAL EXCRETION OF THE GD(III) COMPLEXES OF VARIOUS DTPA-BIS(AMINO ACID DERIVATIVES)

The Gd(III) complexes of Example 26 were introduced into rats and urinary and biliary and/or fecal excretion was determined substantially as described in Examples 22–13. The excretion data indicated that all of these contrast agents underwent hepatobiliary and renal uptake and suggested that they would be useful in MRI.

Gd-DTPA-(L-EtO-PheOH)$_2$ at tracer dose gave values of 1.6%±0.7%, 61.7%±7.6%, and 43.0%±13.9% for residual, urinary and fecal activity, respectively. The corresponding values for a 0.1 mmol/kg dose were 1.8%±0.8%, 71.4%±4.4%, and 29.6%±3.9%. One-hour cumulative urinary and biliary excretion levels after injection of a tracer dose were 45.0%±2.1% and 26.4%±8.4%, respectively. The corresponding values for a dose of 0.1mmol/kg were 55.4%±2.0% and 23.6%±2.2%.

Gd-DTPA-(L-t-Bu-PheOH)$_2$ at tracer dose gave values of 0.9%±0.2%, 33.2%±10.6%, and 71.0%±3.5% for residual, urinary, and fecal activity, respectively. One-hour cumulative urinary and biliary excretion levels after injection of a tracer dose were 18.8%±1.4% and 69.3%±2.0%, respectively.

EXAMPLE 28

MAGNETIC RESONANCE IMAGING USING GD(III) COMPLEXES OF VARIOUS DTPA-BIS (AMINO ACID DERIVATIVES)

The Gd(III) complexes of Example 26 were used as contrast agents in magnetic resonance imaging of a rat, substantially as described in Example 3. The images indicated that all of these contrast agents underwent hepatobiliary and renal uptake and were useful in MRI.

Gd-DTPA-(L-EtO-PheOH)$_2$ at 0.1 mmol/kg dose resulted in the following mean (n=4) contrast enhancement values (as defined in Example 19) in the liver: at 5 minutes, 86%±15%; at 15 minutes, 87%±7%; and at 70 minutes, 52%±3%. The corresponding values for the renal cortex were: at 5 minutes, 204%±49%; at 15 minutes, 137%±9%; and at 70 minutes, 54%±3%. The following values were obtained for skeletal muscle: at 5 minutes, 32%±3%; at 15 minutes, 13%±9%; and at 70 minutes, 6%±6 %.

Gd-DTPA-(L-t-Bu-PheOH)$_2$ at 0.1 mmol/kg dose resulted in the following contrast enhancement (per cent change in signal intensity) values in the liver: at 5 minutes, 104%±5%; at 15 minutes, 80%±10%; and at 70 minutes, 30%±39%. The corresponding values for the renal cortex were: at 5 minutes, 126%±51%; at 15 minutes, 94%±18%; and at 70 minutes, 52 %±21%. The following values were obtained for skeletal muscle: at 5 minutes, 52%±18%; at 15 minutes, 54%±17% and at 60 minutes, 21%±22%.

While some embodiments of the invention have been shown and described herein, it will become apparent to those skilled in the art that various modifications and changes can be made in the amino acid containing hepatobiliary or cardiac contrast agents or their use in magnetic resonance imaging of the torso or abdomen of a mammal without departing from the spirit and scope of the present invention. All such modifications and changes coming within the scope of the appended claims are intended to be carried out thereby.

We claim:

1. A method of preparing a polydentate amino-acyl-type chelator (L$^1$) which method comprises:

(a) contacting an anhydride of the following formula:

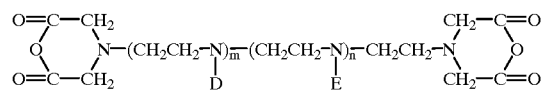

wherein D and E are CH$_2$(C=O)OR$^1$, with an amino acid of the structure H$_2$N—CH(R)—(C=O)OH, an ester of the structure H$_2$NCH(R)—(C=O)OR$^1$ or an amide of the structure H$_2$N—CH(R)—(C=O)—N(R$^2$)(R$^3$);

wherein each R is independently selected from the group consisting of —K, —W and —K—W, wherein each K is an alkyl group having 1–7 carbon atoms, and each W is independently selected from the group consisting of aryl, substituted aryl, heteroaryl and substituted heteroaryl;

R$^1$, R$^2$ and R$^3$ are independently selected from hydrogen (i.e. the acid), alkyl having 1–7 carbon atoms, cyclohexyl, phenyl, benzyl, and 1- or 2-naphthyl, and m is selected from 0, 1, 2 or 3, and n is selected from 0 or 1; and (b) removing the solvent and recovering a polydentate amino-acyl-type chelator of the following formula:

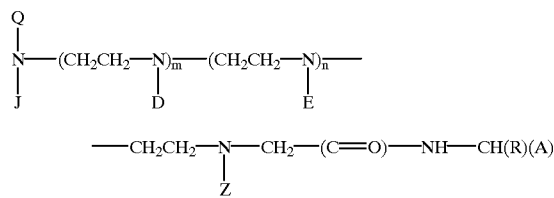

wherein Q, J and Z are each independently selected from the group consisting of —CH$_2$(C=O)OR$^1$ and —CH$_2$—(C=O)—NH—CH(P)(A), and D and E are as defined above;

wherein each R is independently selected from the group consisting of —K, —W and —K—W, as defined above;

wherein the catom in —CH(R)(A) of each of the —CH$_2$—(C=O)—NH—CH(R)(A) moieties is a chiral center of the D or L configuration and, when the contrast agent comprises a multitude of such moieties, the multitude of chiral centers are either of the D or the L configuration or a mixture thereof; and each A is a carbonyl-containing moiety independently selected from the group consisting of —(C=O)OR$^1$ and —(C=O)—N(R$^2$)(R$^3$), wherein R$^1$, R$^2$ and R$^3$ are independently selected from the group consisting of hydrogen (i.e. the acid), alkyl having 1–7 carbon atoms, cyclohexyl, phenyl, benzyl, 1-naphthyl and 2-naphthyl; and m and n are as defined above.

2. The method of claim 1, wherein the anhydride is contacted with an amino acid of the structure:

H$_2$N—CH(R)—(C=O)OH.

3. The method of claim 1, wherein the anhydride is contacted with an ester of the structure:

H$_2$N—CH(R)—(C=O)OR$^1$.

4. The method of claim 1 wherein the anhydride is contacted with an amide of the structure:

H$_2$N—CH(R)—(C=O)—N(R$^2$)(R$^3$).

5. The method of claim 1, wherein the contacting step (a) is conducted in an anhydrous dipolar aprotic solvent at a temperature of between about 50 and 150° C.

6. The method of claim 5, wherein the dipolar aprotic solvent is independently selected from dimethylsulfoxide or mixtures thereof.

7. The method of claim 1, wherein m is 1 and n is 0.

8. The method of claim 1, wherein at least one R is selected from the group consisting of —W and —K—W.

9. The method of claim 1 wherein at least one R comprises an aryl group substituted with 1 to 3 groups independently selected from alkyl having 1–7 carbon atoms, halo, haloalkyl having 1–7 carbon atoms, hydroxyl, carboxyl, acetoxyl, alkoxyl having 1–7 carbon atoms, amino, nitro, nitroso, sulfonyl and thio.

10. The method of claim 8 wherein aryl is independently selected from phenyl and naphthyl, and wherein substituted aryl is independently selected from substituted phenyl and substituted naphthyl.

11. The method of claim 8, wherein at least one R is —K—W, wherein K is selected from the group consisting of methylene, ethylene and propylene, and W is substituted phenyl.

12. The method of claim 11, wherein substituted phenyl is substituted with 1 to 3 groups independently selected from hydroxyl, alkyl having 1 to 5 carbon atoms and alkoxyl having 1 to 5 carbon atoms.

13. The method of claim 12, wherein K is methylene and substituted phenyl is selected from the group consisting of hydroxyphenyl, methoxyphenyl, ethoxyphenyl and t-butylphenyl.

14. The method of claim 13, wherein substituted phenyl is selected from the group consisting of p-ethoxyphenyl and p-tert-butylphenyl.

15. The method of claim 8, wherein at least one R comprises a heteroaryl or substituted heteroaryl, wherein heteroaryl is selected from the group consisting of indolyl and imidazolyl and substituted heteroaryl is selected from the group consisting of substituted indolyl and substituted imidazolyl.

16. The method of claim 13, wherein m is 1, n is 0, R is —K—W, K is methylene and W is p-ethoxyphenyl.

17. The method of claim 13, wherein m is 1, n is 0, R is —K—W, K is methylene and W is p-tert-butylphenyl.

18. The method of claim 5, wherein the dipolar aprotic solvent is independently selected from dimethylsulfoxide or mixtures thereof and the heating temperature is between about 90 and 100° C. and the time is between about 2 and 10 hours.

* * * * *

UNITED STATES PATENT AND TRADEMARK OFFICE

CERTIFICATE OF CORRECTION

PATENT NO. : 5,914,097

DATED : June 22, 1999

INVENTOR(S) : David L. White

It is certified that error appears in the above-identified patent and that said Letters Patent is hereby corrected as shown below:

Column 25, line 67, after ")", please insert --,--;
column 26, line 39, please delete "P" and insert --R--;
        line 44, please delete "catom" and insert --C atom";
column 28, line 16, please delete "13" and insert --14--;
        line 18, please delete "13" and insert --14--;
        line 22, after "thereof", please insert --;--.

Signed and Sealed this

Twenty-sixth Day of December, 2000

Attest:

Q. TODD DICKINSON

*Attesting Officer*      *Director of Patents and Trademarks*